(12) United States Patent
Cheng et al.

(10) Patent No.: US 9,586,983 B2
(45) Date of Patent: Mar. 7, 2017

(54) AMPHIPHILIC NANOSHEETS AND METHODS OF MAKING THE SAME

(71) Applicant: The Texas A&M University System, College Station, TX (US)

(72) Inventors: Zhengdong Cheng, College Station, TX (US); Andres F. Mejia, College Station, TX (US); Agustin Diaz, College Station, TX (US); Abraham Clearfield, College Station, TX (US); Mahboobul S Mannan, College Station, TX (US); Ya-Wen Chang, College Station, TX (US)

(73) Assignee: The Texas A&M University System, College Station, TX (US)

( * ) Notice: Subject to any disclaimer, the term of this patent is extended or adjusted under 35 U.S.C. 154(b) by 189 days.

(21) Appl. No.: 14/624,974

(22) Filed: Feb. 18, 2015

(65) Prior Publication Data

US 2015/0299240 A1    Oct. 22, 2015

Related U.S. Application Data

(63) Continuation of application No. 13/848,669, filed on Mar. 21, 2013, now Pat. No. 8,986,641.
(Continued)

(51) Int. Cl.
*C01B 15/16* (2006.01)
*C07F 19/00* (2006.01)
(Continued)

(52) U.S. Cl.
CPC ............. *C07F 19/005* (2013.01); *B01J 19/10* (2013.01); *C01B 25/26* (2013.01); *C01B 25/372* (2013.01);
(Continued)

(58) Field of Classification Search
CPC ..... C07F 19/005; C01B 31/04; C01B 25/372; C01B 31/0423; C01B 33/26;
(Continued)

(56) References Cited

PUBLICATIONS

Boo et al, "Effective Intercalation and Exfoliation of nanoplatelets in Epoxy via Creation of Porous Pathways", J. Phys. Chem. C 111 (28), pp. 10377-10381, 2007.
(Continued)

*Primary Examiner* — Colleen Dunn
*Assistant Examiner* — Haytham Soliman
(74) *Attorney, Agent, or Firm* — Winstead PC

(57) ABSTRACT

In some embodiments, the present invention provides amphiphilic nanosheets that comprise lamellar crystals with at least two regions: a first hydrophilic region, and a second hydrophobic region. In some embodiments, the amphiphilic nanosheets of the present invention also comprise a plurality of functional groups that are appended to the lamellar crystals. In some embodiments, the functional groups are hydrophobic functional groups that are appended to the second region of the lamellar crystals. In some embodiments, the lamellar crystals comprise α-zirconium phosphates. Additional embodiments of the present invention pertain to methods of making the aforementioned amphiphilic nanosheets. Such methods generally comprise appending one or more functional groups to a stack of lamellar crystals; and exfoliating the stack of lamellar crystals for form the amphiphilic nanosheets.

12 Claims, 19 Drawing Sheets

Related U.S. Application Data

(60) Provisional application No. 61/613,668, filed on Mar. 21, 2012.

(51) Int. Cl.
| | |
|---|---|
| *B01J 19/10* | (2006.01) |
| *C01B 25/26* | (2006.01) |
| *C01B 31/04* | (2006.01) |
| *C01B 25/37* | (2006.01) |
| *C01G 23/00* | (2006.01) |
| *C01G 33/00* | (2006.01) |
| *C01B 33/26* | (2006.01) |

(52) U.S. Cl.
CPC .......... *C01B 31/04* (2013.01); *C01B 31/0423* (2013.01); *C01B 31/0438* (2013.01); *C01B 33/26* (2013.01); *C01G 23/003* (2013.01); *C01G 33/00* (2013.01); *C01P 2002/82* (2013.01); *C01P 2002/85* (2013.01); *C01P 2002/88* (2013.01); *C01P 2004/03* (2013.01); *C01P 2004/04* (2013.01); *C01P 2004/24* (2013.01)

(58) Field of Classification Search
CPC ..... C01B 31/0438; C01B 25/26; C01G 33/00; C01G 23/003; B01J 19/10; C01P 2002/88; C01P 2004/03; C01P 2002/85; C01P 2004/04; C01P 2002/82; C01P 2004/24
USPC ........................................................ 423/306
See application file for complete search history.

(56) References Cited

PUBLICATIONS

Sun, Luyi et al, "Preparation of ∝-zirconium Phosphate Nanoplatelets with Wide Variations in Aspect Ratios", New J. Chem., vol. 31, pp. 39-43, 2007.

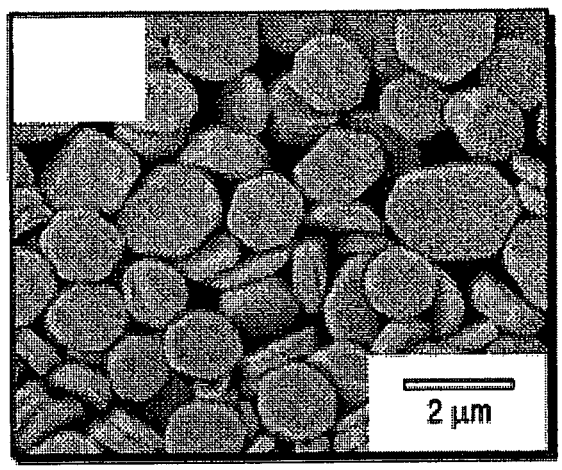
FIG. 2A
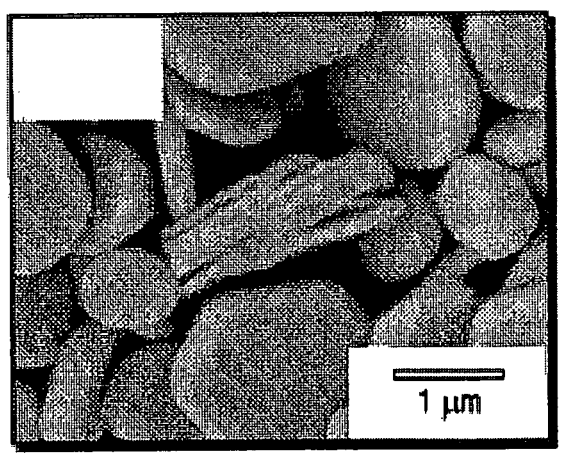
FIG. 2B
Fig. 2

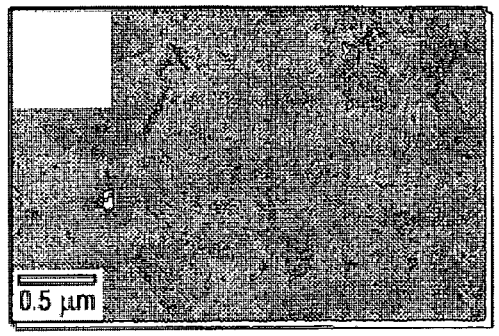
FIG. 4A
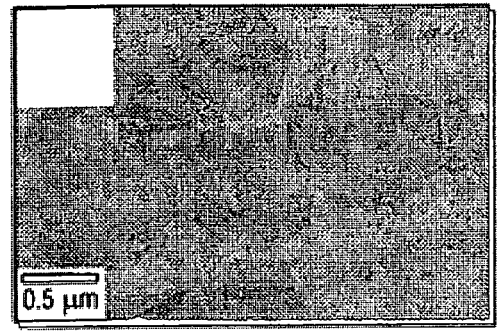
FIG. 4B
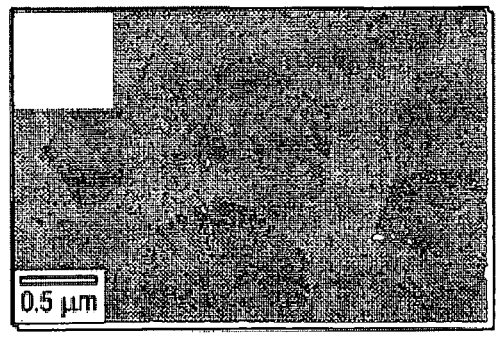
FIG. 4C
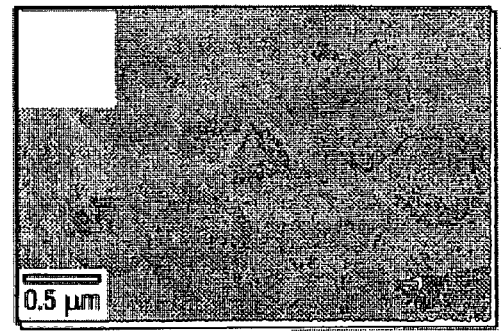
FIG. 4D
Fig. 4

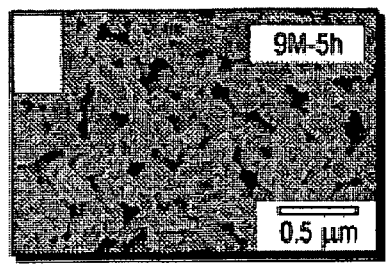
FIG. 5A
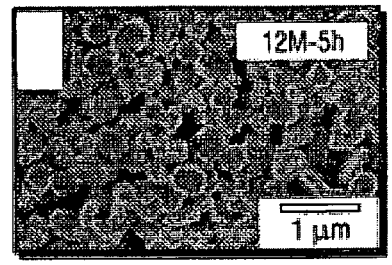
FIG. 5B
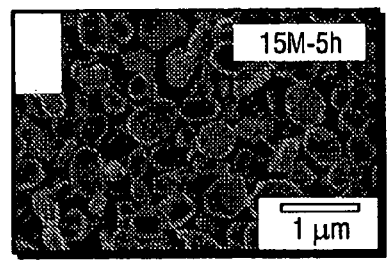
FIG. 5C
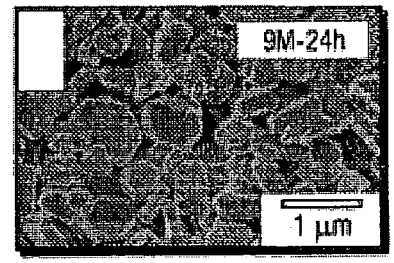
FIG. 5D
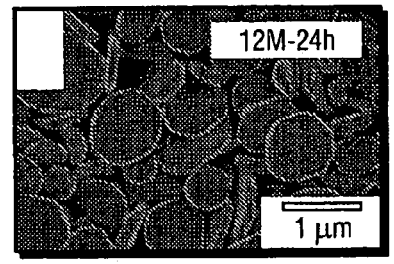
FIG. 5E
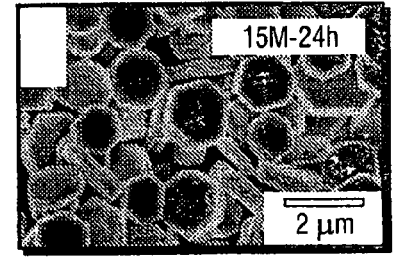
FIG. 5F
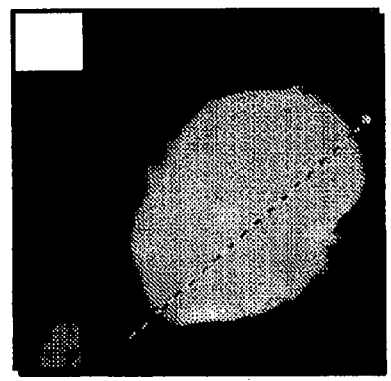
FIG. 5H
Fig. 5

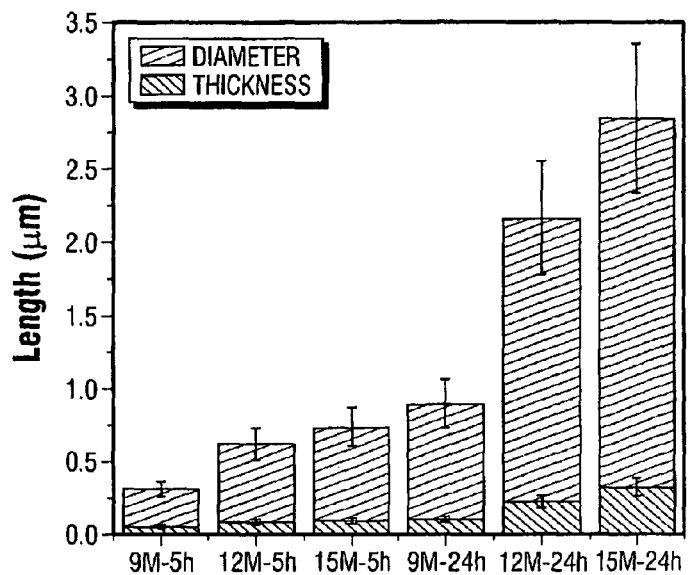
FIG. 5G
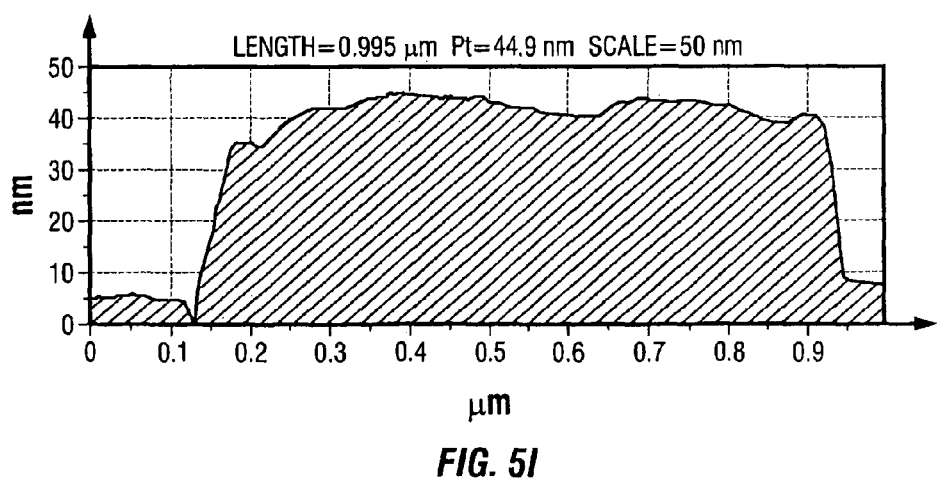
FIG. 5I
Fig. 5

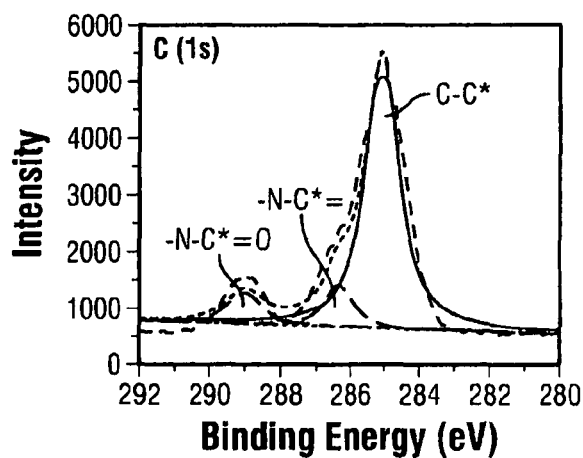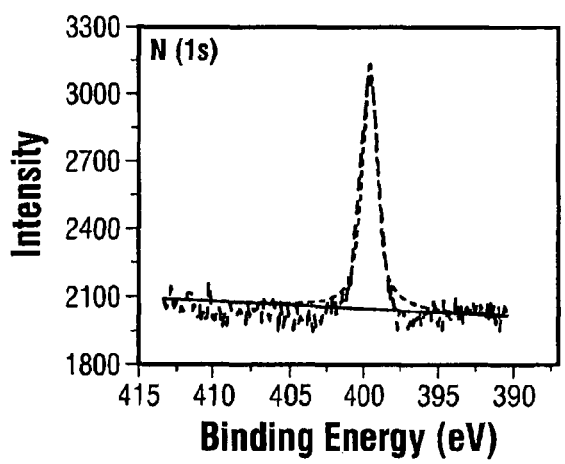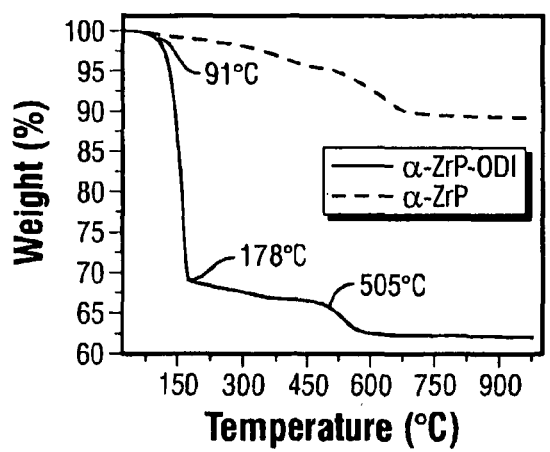
Fig. 8

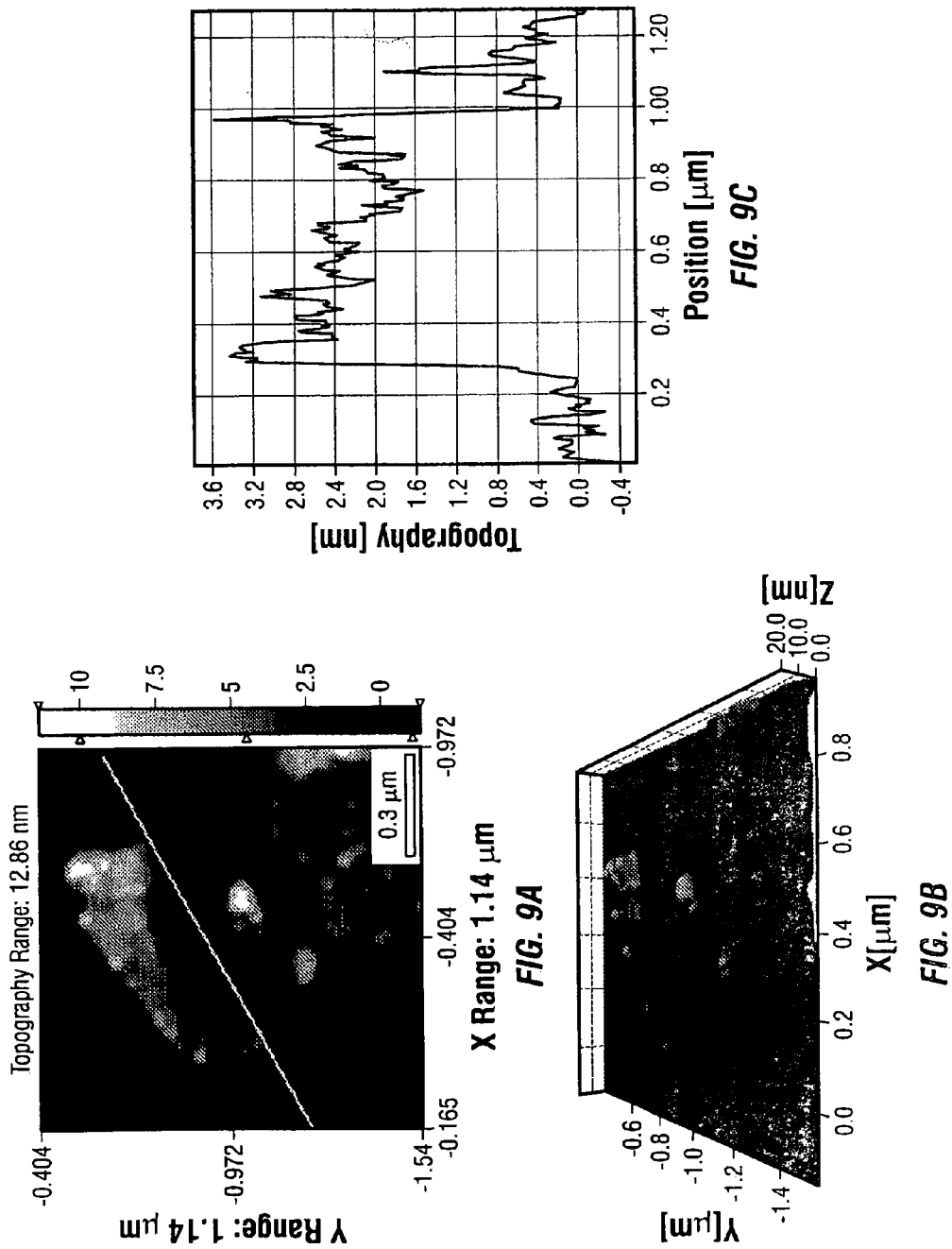

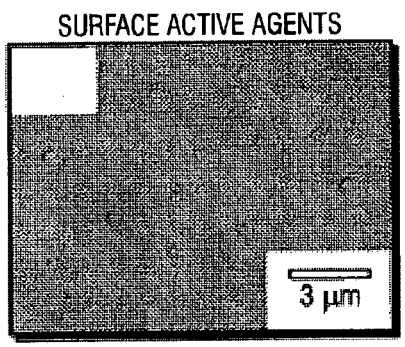
FIG. 10A
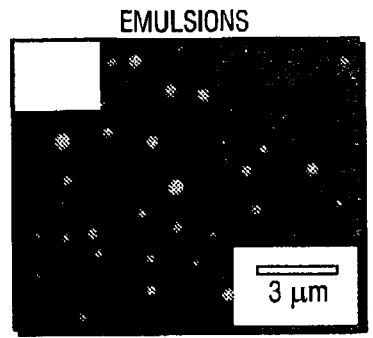
FIG. 10B
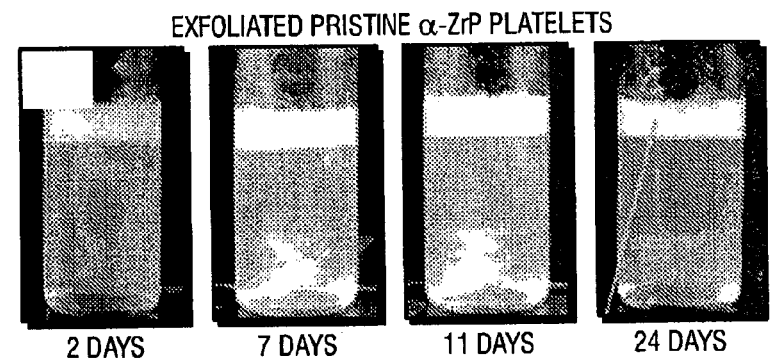
FIG. 10C
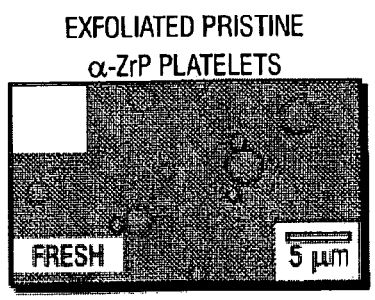
FIG. 10D
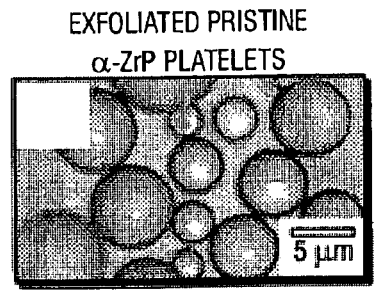
FIG. 10E
Fig. 10

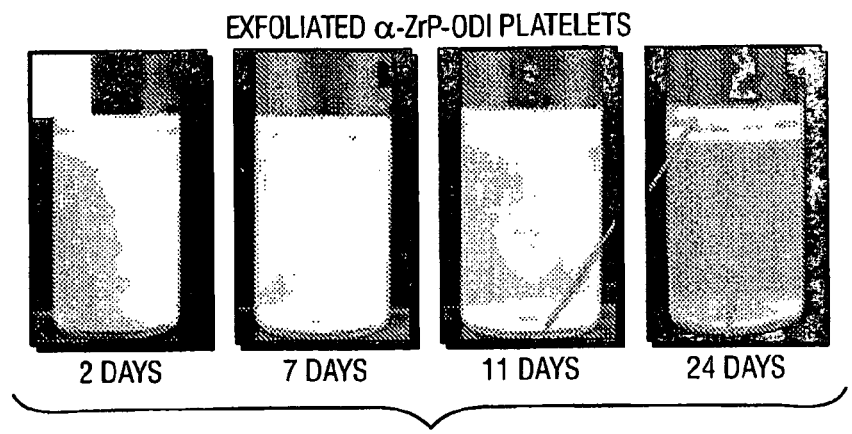
FIG. 10F
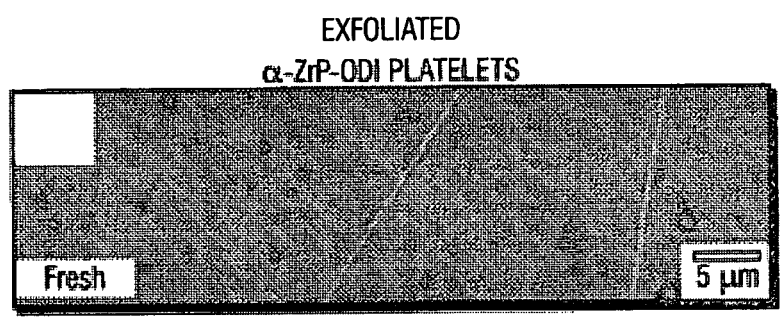
FIG. 10G
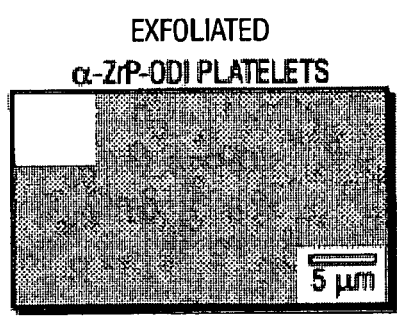
FIG. 10H
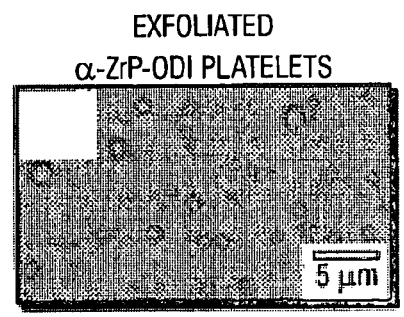
FIG. 10I
Fig. 10

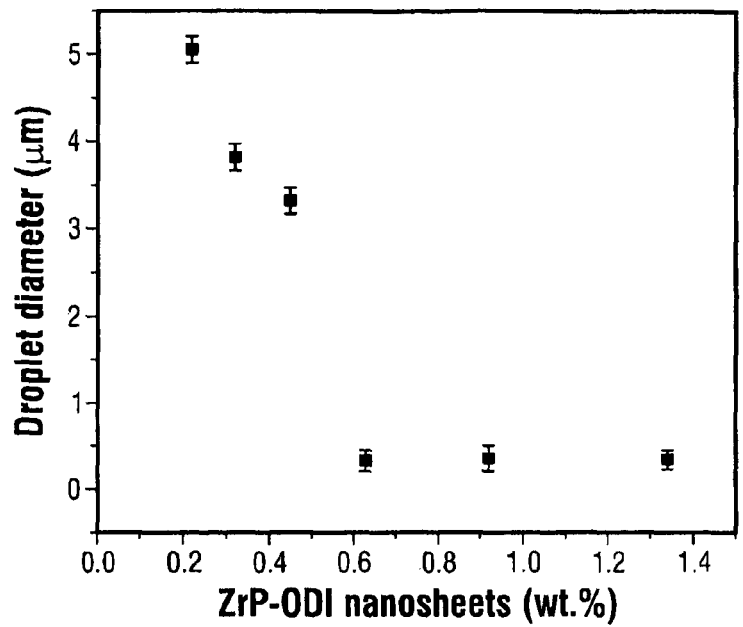
FIG. 11A
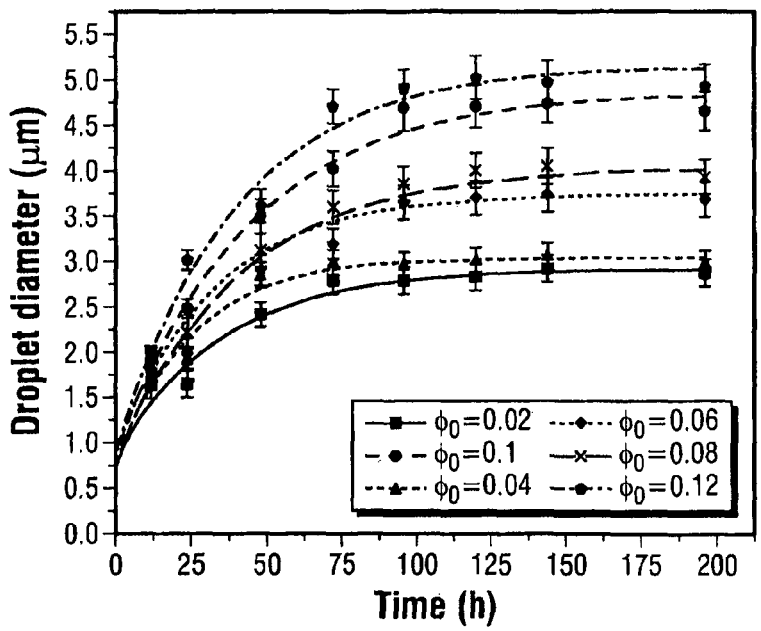
FIG. 11B
Fig. 11

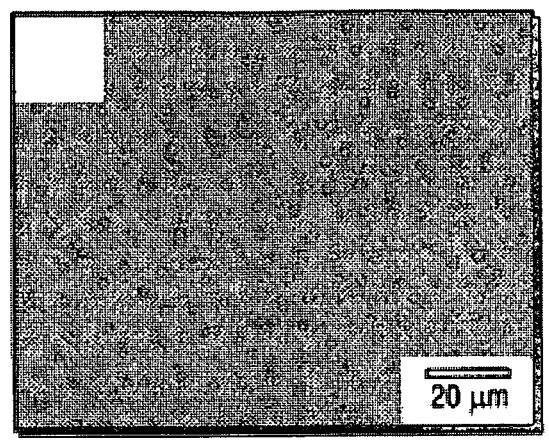
FIG. 12A
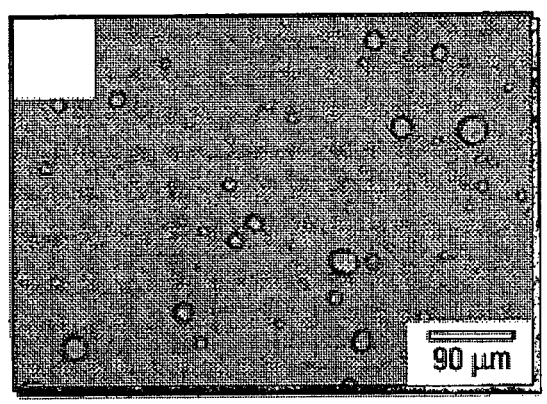
FIG. 12B
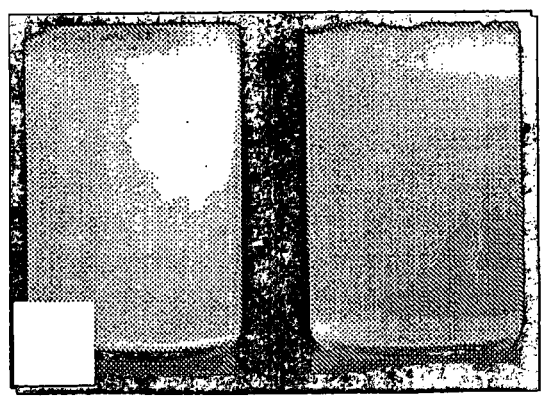
FIG. 12C
Fig. 12

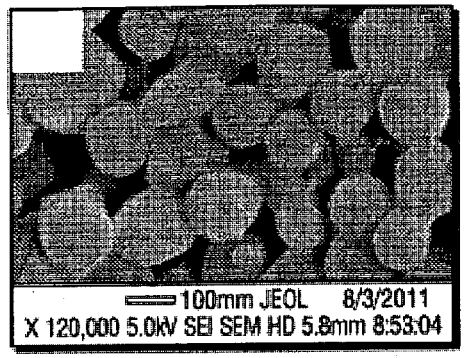
FIG. 14A
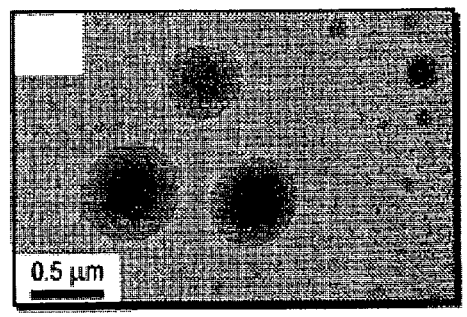
FIG. 14B
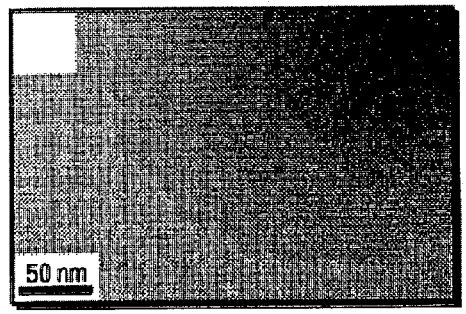
FIG. 14C
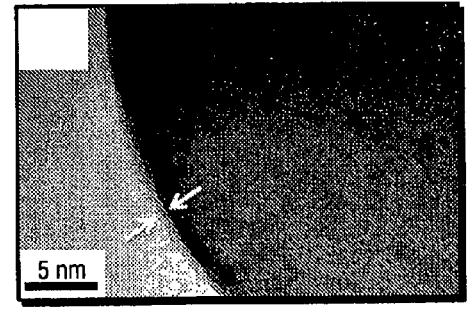
FIG. 14D
Fig. 14

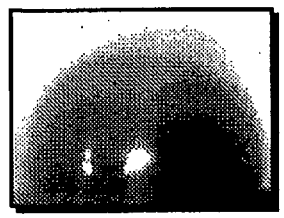
FIG. 16A
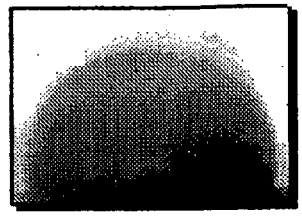
FIG. 16B
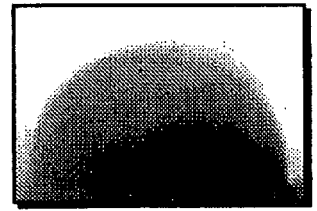
FIG. 16C
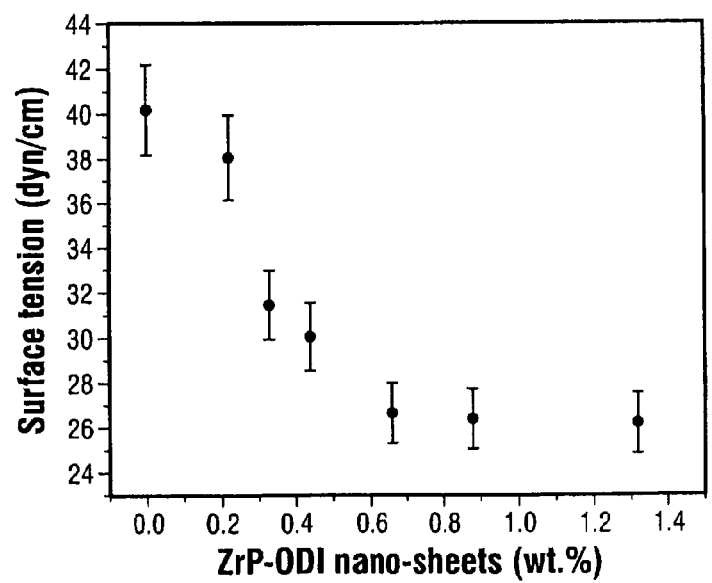
FIG. 16D
Fig. 16

AMPHIPHILIC NANOSHEETS AND METHODS OF MAKING THE SAME

CROSS-REFERENCE TO RELATED APPLICATIONS

The present application is a continuation of U.S. patent application Ser. No. 13/848,669 filed Mar. 21, 2013. U.S. patent application Ser. No. 13/848,669 claims the benefit of, and incorporates by reference for any purpose the entire disclosure of, U.S. Provisional Patent Application No. 61/613,668 filed Mar. 21, 2012.

STATEMENT REGARDING FEDERALLY SPONSORED RESEARCH

This invention was made with government support under Grant Nos. DMR-1006870 and DMR-0652166, both awarded by the National Science Foundation. The government has certain rights in the invention.

BACKGROUND OF THE INVENTION

Current surfactants have numerous limitations in terms of solubility, durability and effectiveness. Current methods of making surfactants also have limitations in terms of efficiency and mass production. Therefore, a need exists for the development of more effective surfactants and methods of making them.

BRIEF SUMMARY

In some embodiments, the present invention provides amphiphilic nanosheets that comprise lamellar crystals with at least two regions: a first hydrophilic region, and a second hydrophobic region. In some embodiments, the amphiphilic nanosheets of the present invention also comprise a plurality of functional groups that are appended to the lamellar crystals. In some embodiments, the amphiphilic nanosheets have thicknesses ranging from about 0.5 nm to about 5 nm, and diameters ranging from about 10 nm to about 10 μm.

In some embodiments, the functional groups include at least one of alkyl groups, aryl groups, amine groups, amide groups, ester groups, epoxy groups, carbonyl groups, alcohol groups, urethanes, isocyanates, aminosilanes, and combinations thereof. In some embodiments, the functional groups are hydrophobic functional groups that are appended to the second region of the lamellar crystals.

In some embodiments, the lamellar crystals include at least one of clays, zirconium phosphates, titanium phosphates, hafnium phosphates, silicon phosphates, germanium phosphates, tin (IV) phosphates, lead (IV) phosphates, niobates, titanates, organic crystals, graphites, graphenes, polyhydroxybutyric acids, and combinations thereof. In some embodiments, the lamellar crystals comprise a-zirconium phosphates.

Additional embodiments of the present invention pertain to methods of making the aforementioned amphiphilic nanosheets. Such methods generally comprise appending one or more functional groups to a stack of lamellar crystals and exfoliating the stack of lamellar crystals to form the amphiphilic nanosheets.

In some embodiments, the appending step includes the covalent linkage of one or more functional groups to the stack of lamellar crystals. In more specific embodiments, the appending step includes covalently linking hydrophobic functional groups to the second region of the lamellar crystals in order to make the region hydrophobic.

In some embodiments, the exfoliating step includes sonicating the stack of lamellar crystals. In some embodiments, the exfoliating step includes exposing the stack of lamellar crystals to an ionic composition, such as tetra-(n-butylammonium) hydroxide.

The amphiphilic nanosheets of the present invention have numerous applications. For instance, in some embodiments, the amphiphilic nanosheets can be used as surfactants in various settings.

BRIEF DESCRIPTION OF THE FIGURES

FIGS. 2A-2C show α-zirconium phosphate (α-ZrP) crystals. FIG. 2A is a scanning electron micrograph (SEM) image of the crystals. FIG. 2B is a zoomed in view of the crystals showing cracks along the lamellar layers. FIG. 2C depicts structures of the alpha phase of the α-ZrPs.

FIG. 4 shows transmission electron micrograph (TEM) images of several non-modified α-ZrP nanosheets.

FIGS. 5A-5I summarize various properties of pristine α-zirconium phosphate crystals. FIGS. 5A-5F show SEMs of different α-ZrP sizes synthesized via the hydrothermal method at 200° C. under different conditions (phosphoric acid concentration-reaction time): (FIG. 5A) 9M-5 h, (FIG. 5B) 12M-5 h, (FIG. 5C) 15M-5 h, (FIG. 5D) 9M-24 h, (FIG. 5E) 12M-24 h, and (FIG. 5F) 15M-24 h. FIG. 5G summarizes the quantification of the diameter (gray bar) and the thickness (black bar) of the α-ZrP crystals. FIG. 5H shows an atomic force microscope (AFM) contact mode topography image of a pristine α-ZrP crystal fabricated using 9M phosphoric acid for 24 h over a Si(100) surface modified with 3-aminopropyl trichlorosilane (APTES). FIG. 5I shows section analysis for the cross-section white line seen in FIG. 5H, which gives a thickness of around 38 nm.

FIGS. 8A-8C show X-ray photoelectron spectroscopy (XPS) and thermogravimetric analysis (TGA) spectra of the product obtained from the reaction of ODI with α-ZrP. FIG. 8A shows that the de-convolution of the C1s spectrum exhibits three peaks, consistent with the presence of the N—C(=0)- and carbon atoms. FIG. 8B shows the N1s spectra. FIG. 8C shows the thermal stability of pristine α-ZrP (blue line) and α-ZrP grafted with ODI (green line) analyzed by TGA.

FIGS. 9A-9C show atomic force microscopy (AFM) contact mode topography image and section analysis of an amphiphilic α-ZrP-ODI nanosheet over a Si(100) surface modified with octadecyltrichlorosilane (OTS). FIGS. 9A and 9B show 2D and 3D topography images, respectively. FIG. 9C shows a section analysis, which indicates a thickness of around 2.8 nm (0.63 nm of a α-ZrP monolayer and 2.17 nm of the aliphatic chain) for the cross-section white line seen in FIG. 9A.

FIGS. 10A-10I provide data related to the characterization of stable emulsions stabilized by α-ZrP-ODI nanosheets and unstable emulsions using non-modified α-ZrP nanosheets. Representative (FIG. 10A) optical micrograph and (FIG. 10B) confocal laser scanning micrograph of oil-water (o/w) emulsions using α-ZrP-ODI as surface-active agents are shown. In addition, FIG. 10C provides observation of o/w emulsions stabilized by non-modified α-ZrP monolayers. The emulsion coalesced and quickly creamed. FIG. 10D shows optical micrographs of the o/w emulsion right after emulsification and (FIG. 10E) after 24 days, which indicates that non-modified α-ZrP nanosheets are not good emulsifiers due to the observed coalescence. FIG. 10F shows the creaming of o/w emulsions stabilized by α-ZrP-ODI nanosheets. The emulsion presents less creaming compared to FIG. 10C due to the less degree of coalescence. FIG. 10G is a micrograph showing the oil-in-water droplets after emulsifiying. FIG. 10H is an o/w emulsion micrograph from the top and (FIG. 10I) from the middle after 24 days, where no coalescence was observed. Pictures of (FIGS. 10A, 10D-E, and 10G-I) were taken using a Nikon microscope TE-2000U with 20× magnification, FIG. 10B was taken using a Leica confocal microscope TCS SP5 with magnification of 100×. Digital photographs shown in FIG. 10C and FIG. 10F were taken using a Sony DSC-220W digital still camera.

FIGS. 11A-11B show various data related to toluene-in-water emulsions. FIG. 11A shows toluene-in-water emulsion droplet diameter as a function of α-ZrP-ODI nanosheet concentration after one week. The toluene volume fraction is $\Phi_o=0.085$. FIG. 11B shows droplet diameter of toluene-in-water emulsions as a function of time. The concentration of α-ZrP-ODI nanosheets is 0.45 wt %.

FIGS. 12A-12C show toluene-in-water emulsions stabilized by α-ZrP-ODI and non-modified α-ZrP nanosheets where toluene concentration was $\Phi_o=0.085$. FIG. 12A shows a micrograph of uniform toluene-in-water droplets stabilized by α-ZrP-ODI nanosheets. The diameter of the droplets is 3.05±0.42 μm. FIG. 12B shows a micrograph of polydispersed toluene-in-water emulsion droplets stabilized by non-modified α-ZrP nanosheets. FIG. 12C shows toluene-in-water emulsions stabilized by non-modified α-ZrP (right) showing strong creaming due to large drop size and stabilized by α-ZrP-ODI nanosheets (left) with a less creaming effect. The picture is taken at 200 h after emulsification.

FIGS. 14A-14D show images of Pickering miniemulsions of styrene-in-water. FIG. 14A is an SEM image of platelet-armored-polystyrene particles. FIGS. 14B-D are TEM images of platelet-armored polystyrene particles.

FIG. 16 shows contact angle measurements for seven different samples at different α-ZrP-ODI nanosheet concentrations.

DETAILED DESCRIPTION OF EXEMPLARY EMBODIMENTS

Figure 1A:
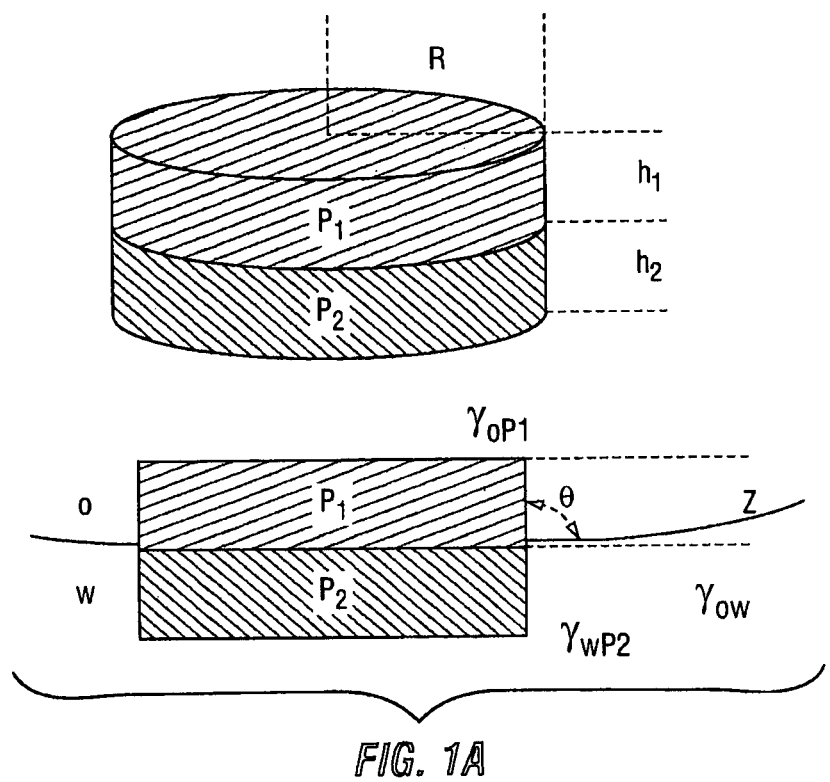
FIGS. 1A-1B provide illustrations of a disk-shaped Janus particle (FIG. 1A) and its interfacial adsorption (FIG. 1B).

It is to be understood that both the foregoing general description and the following detailed description are exemplary and explanatory only, and are not restrictive of the invention, as claimed. In this application, the use of the singular includes the plural, the word "a" or "an" means "at least one", and the use of "or" means "and/or", unless specifically stated otherwise. Furthermore, the use of the term "including", as well as other forms, such as "includes" and "included", is not limiting. Also, terms such as "element" or "component" encompass both elements or components comprising one unit and elements or components that comprise more than one unit unless specifically stated otherwise.

The section headings used herein are for organizational purposes only and are not to be construed as limiting the subject matter described. All documents, or portions of documents, cited in this application, including, but not limited to, patents, patent applications, articles, books, and treatises, are hereby expressly incorporated herein by reference in their entirety for any purpose. In the event that one or more of the incorporated literature and similar materials defines a term in a manner that contradicts the definition of that term in this application, this application controls.

Amphiphilic particles are both hydrophilic and hydrophobic. Acting as surfactants, they are able to stabilize liquid-liquid interfaces to form Pickering emulsions (emulsions stabilized by particles). Two types of amphiphilic particles are the Janus and Gemini particles. Janus particles generally have two hemispheres or halves with distinguishable differences in chemical properties. Currently, there are several methods to prepare Janus particles. For example, Janus particles can be obtained from double-emulsion droplets using microfluidics, electrohydrodynamic jetting of parallel polymer solutions, metal coating, and a hierarchical self-assembly process. Janus particles are also building blocks for supra-particular assemblies based on their anisotropy, which offers a gamut of other applications, such as drug delivery agents, photonic crystals, electronics, and photolithography. Janus particles are strongly adsorbed to interfaces, where they act as surfactants for the formation of stable Pickering emulsions.

Gemini molecular surfactants can be described as molecules having a long hydrocarbon sequence, followed by a charged group (cationic, anionic, or nonionic), a spacer (rigid or flexible), a second charged group, and another hydrocarbon chain segment. Regular surfactants are characterized by their critical micelle concentrations (CMCs), above which the molecules prefer to join the micelle rather than the interface. Gemini molecules are well known to possess lower CMC values than do the surfactants of equivalent chain length, making them more efficient in lowering surface tension.

Although Janus particles function as regular surfactants in terms of their function in stabilizing Pickering emulsions (as the counterpart to the Gemini surfactants), the Gemini particles have not yet been fabricated. Furthermore, there is a need to create more effective viscoelastic surfactants that combine viscosity with surfactancy. The present invention addresses these needs by demonstrating the fabrication of surface and edge-modified amphiphilic nanosheets by the use of lamellar crystals.

As set forth in more detail below, the methods and compositions of the present invention have numerous variations. More specific and non-limiting embodiments of the present invention will now be described in more detail.

Amphiphilic Nanosheets

In some embodiments, the present invention pertains to amphiphilic nanosheets. Such nanosheets generally include lamellar crystals with at least two regions: a first hydrophilic region and a second hydrophobic region. In some embodiments, the amphiphilic nanosheets of the present invention also include one or more functional groups that are appended to the lamellar crystals.

As set forth in more detail below, various lamellar crystals may be utilized in the amphiphilic nanosheets of the present invention. Likewise, various functional groups may be appended to various regions of the lamellar crystals.

Lamellar Crystals

Lamellar crystals generally refer to polycrystalline compositions that are in the form of thin sheets (e.g., sheets with thicknesses ranging from about 0.5 nm to about 5 nm). The amphiphilic nanosheets of the present invention may include various lamellar crystals. In some embodiments, the lamellar crystals include, without limitation, clays, zirconium phosphates ($\alpha$-ZrP), titanium phosphates ($\alpha$-TIP), hafnium phosphates ($\alpha$-HfP), silicon phosphates ($\alpha$-SiP), germanium phosphates ($\alpha$-GeP), tin (IV) phosphates ($\alpha$-SnP), lead (IV) phosphates ($\alpha$-PbP), niobates, titanates, organic crystals, graphites, graphenes, polyhydroxybutyric acids, and combinations thereof.

In more general embodiments, the lamellar crystals of the present invention include crystals of atoms from columns IVB, VIA, and VA of the periodic table of elements. In some embodiments, such atoms may also be associated with P, O and H.

In various embodiments, the lamellar crystals of the present invention can stack into layered compounds and be exfoliated into layers. In some embodiments, the lamellar crystals of the present invention can have various regions with different properties. For instance, in some embodiments, the lamellar crystals of the present invention may have one region that is hydrophilic and another region that is hydrophobic. In some embodiments, such regions may be surfaces, edges, or combinations of surfaces and edges. For instance, in more specific embodiments, the lamellar crystals may have one surface that is hydrophilic and another opposite surface that is hydrophobic.

In various embodiments, different functional groups may be appended to different regions of the lamellar crystals in order to confer the different properties.

Functional Groups

Various regions of the lamellar crystals of the present invention may be functionalized with various functional groups. Such functional groups may include, without limitation, cationic functional groups, anionic functional groups, nonionic functional groups, and combinations thereof. In some embodiments, the functional groups are monomeric molecules. In some embodiments, the functional groups are polymers. In various embodiments, the lamellar crystals may be covalently or non-covalently functionalized with such functional groups.

Non-limiting examples of functional groups that may be appended to lamellar crystals may include, without limitation, alkyl groups, aryl groups, amine groups, amide groups, ester groups, epoxy groups, carbonyl groups, alcohol groups, urethanes, isocyanates, silanes, aminosilanes, and combinations thereof. In more specific embodiments, the functional groups include, without limitation, 3-aminopropyl trichlorosilane (APTES), octadecyl isocyanate, 3-(trethoxysilyl)propyl isocyanate, 4-(trechlosilyl)butyronitrile, trichloro(phenyl)silane, 3-(methacryloyloxy)propyl trimethoxysilane (MOPT), trans-1,4-cyclohexylene diisocyanate, 1,6-diisocyanatohexane, and combinations thereof. In more specific embodiments, the functional groups include octadecyl isocyanate (ODI).

Functional groups may be appended to various regions of lamellar crystals. In some embodiments, the functional groups may be appended to one or more surfaces or edges of the lamellar crystals. Furthermore, different regions of lamellar crystals may have functional groups with different properties. For instance, in some embodiments, a surface of a lamellar crystal may be functionalized with hydrophilic functional groups while another surface of the lamellar crystal may be functionalized with hydrophobic functional groups. Such hydrophilic and hydrophobic functional groups can in turn confer hydrophilic and hydrophobic properties on the respective surfaces. In more specific embodiments, a surface or region of a lamellar crystal may be functionalized with hydrophobic functional groups while other surfaces or regions remain unfunctionalized.

In some embodiments, the functional groups on the surfaces or edges of lamellar crystals can be further chemically reacted to extend and/or change functions or properties. In various embodiments, each surface, edge or region of lamellar crystals may also have multiple functional groups with different properties. In more specific embodiments, the lamellar crystals may have functional groups on surfaces, edges or regions that have a long hydrocarbon sequence, followed by a charged group (cationic, anionic, or nonionic), a spacer (rigid or flexible), a second charged group, and another hydrocarbon chain segment. For lamellar crystals that form Janus platelets, top and bottom surfaces of the plates may be functionalized with chemically different functional groups (e.g., hydrophilic and hydrophobic functional groups) in some embodiments. For lamellar crystals that form Gemini platelets, the functional groups may be attached to the edges.

Properties

The formed amphiphilic nanosheets of the present invention can also have various properties and arrangements. For instance, the amphiphilic nanosheets can have various sizes, widths, thicknesses, and crystallinities. Furthermore, the size distribution can be monodisperse or polydisperse.

In some embodiments, the amphiphilic nanosheets of the present invention may have thicknesses that range from about 0.5 nm to about 5 nm. In more specific embodiments, the amphiphilic nanosheets of the present invention may have thicknesses that range from about 0.5 nm to about 5 nm. In further embodiments, the amphiphilic nanosheets of the present invention have a thickness of about 2.2 nm.

In some embodiments, the amphiphilic nanosheets of the present invention may have diameters that range from about 10 nm to about 10 µm. In more specific embodiments, the amphiphilic nanosheets of the present invention have a diameter of about 1 µm. In more specific embodiments, the amphiphilic nanosheets of the present invention may have diameters of about 20 nm and thicknesses of about 2-3 nm. In further embodiments, such amphiphilic nanosheets may include $\alpha$-ZrP crystals.

The amphiphilic nanosheets of the present invention may also have various surface areas. For instance, in some embodiments, the amphiphilic nanosheets of the present invention (such as $\alpha$-ZrP nanosheets) may have surface areas that range from about 1 $m^2g^{-1}$ to about 200 $m^2g^{-1}$.

The amphiphilic nanosheets of the present invention may also have various aspect ratios. For instance, in some embodiments, the amphiphilic nanosheets of the present invention (such as α-ZrP nanosheets) may have aspect ratios that range from about 3500 to about 10.

The amphiphilic nanosheets of the present invention may also be capable of self assembly. Furthermore, the amphiphlic nanosheets of the present invention may have various arrangements. For instance, in some embodiments, the amphiphilic nanosheets of the present invention may be arranged as stacks of nanosheets, individual sheets, or combinations thereof.

As also set forth previously, the amphiphilic nanosheets of the present invention can have different regions with different properties (e.g., edges or surfaces with hydrophobic and/or hydrophilic properties). As set forth in more detail below, such different properties provide numerous advantages.

Methods of Making Amphiphilic Nanosheets

Figure 3:
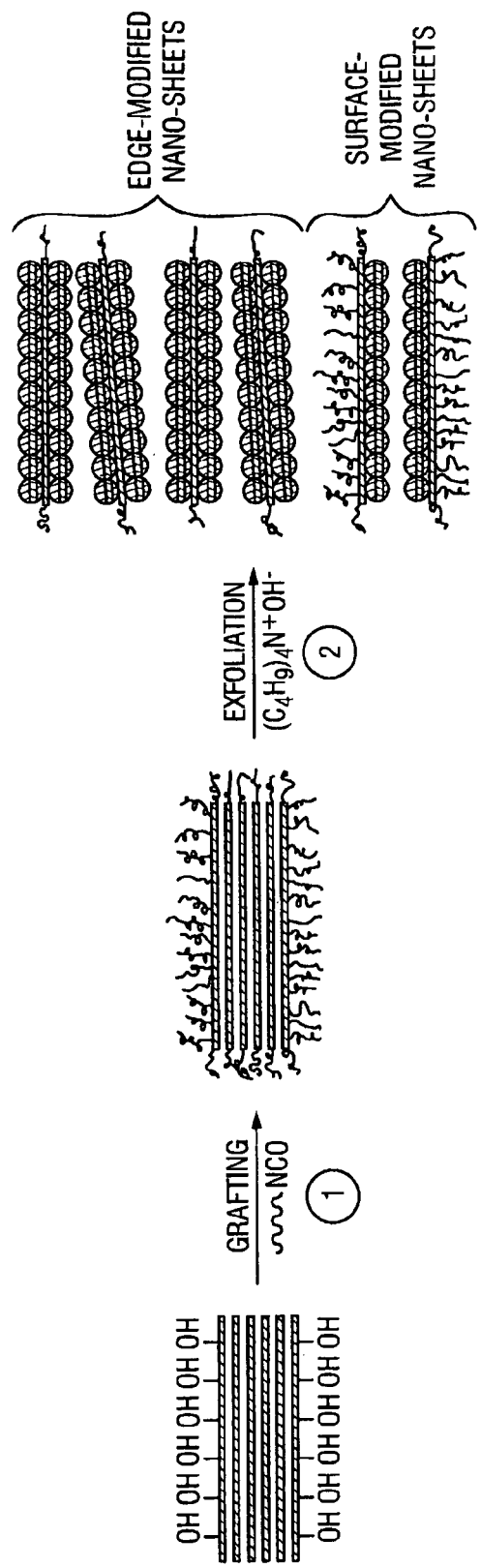
FIG. 3 provides a two dimensional schematic representation of the fabrication of thin-surface and edge-modified amphiphilic nanosheets. The initial step consists of the grafting of a coupling agent over the surface of the α-ZrPs. Subsequently, the exfoliation of the crystals is carried out to obtain the surface and edge-modified nanosheets from their outer and inner layers, respectively.

Additional embodiments of the present invention pertain to methods of making the amphiphilic nanosheets of the present invention. In some embodiments that are depicted in FIG. 3, the method comprises: (1) appending one or more functional groups to a stack of lamellar crystals; and (2) exfoliating the stack of lamellar crystals to form the amphiphilic nanosheets. In some embodiments, the formed nanosheets comprise at least two regions: a first hydrophilic region and a second hydrophobic region. As set forth below, various methods may be used to append functional groups to lamellar stacks and exfoliate the lamellar crystals.

Appending Functional Groups

Various methods may be utilized to append functional groups to lamellar crystals. In some embodiments, the appending includes the covalent linkage of one or more functional groups to the lamellar crystals. In more specific embodiments, the appending includes the covalent linkage of functional groups to one or more edges of the lamellar crystals. In further embodiments, the appending may include the covalent linkage of functional groups to one or more surfaces of the lamellar crystals.

In some embodiments, the lamellar crystals are in stacked form during functionalization. See, e.g. FIG. 3. In such embodiments, the functionalization may be site specific towards a surface or an edge. Thus, in some embodiments, such methods may be used to develop site-specific chemical reactions to functionalize the surfaces of lamellar crystals to be hydrophilic on one side (e.g., with hydrophilic functional groups, such as $HPO_4$ or no functional groups) and hydrophobic on the other side (e.g., with hydrophobic functional groups, such as phenyl groups).

In addition, various moieties and functional groups on lamellar crystals may be utilized for functionalization. For instance, as depicted in FIG. 3, OH groups on the surface of lamellar crystals can be readily used to carry out the chemical reactions. Furthermore, in various embodiments, some of the OH groups may be selectively protected and used later for labeling or other needs. Hence, complex structures can be fabricated on the lamellar crystals.

Exfoliating Lamellar Crystals

In cases where stacked lamellar crystals are functionalized, various methods may also be used to exfoliate the stacked and functionalized lamellar crystals into individual sheets. In some embodiments, the exfoliating includes sonicating the stack of lamellar crystals. In some embodiments, the exfoliating includes exposing the stack of lamellar crystals to an ionic composition, such as tetra-(n-butylammonium) hydroxide ($TBA^+OH^-$). In some embodiments, exfoliation may involve both sonication and exposure to ionic compositions.

The aforementioned methods may also have numerous variations. For instance, in some embodiments, a subsequent functionalization step (as previously described) may also be carried out after an exfoliation step. In further embodiments, the cycle of functionalization and exfoliation may be repeated numerous times with different functional groups to form staged materials, where the surfaces of the lamellar crystals in each layer may be individually functionalized with the same or different functional groups. Thus, in various embodiments, lamellar crystals with different functional groups on each layer may be formed. For instance, in some embodiments, lamellar crystals with a hydrophobic layer (with phenyl groups) and a hydrophilic layer (with $HPO_4$ groups) may be formed. The hydrophobic group may then be functionalized, and the hydrophilic group exfoliated.

The methods of the present invention also provide high yield rates for the production of amphiphilic nanosheets, which can be close to 100% theoretically. Such methods can also be used to mass produce amphiphilic nanosheets.

Advantages and Applications

The aforementioned methods of making amphiphilic nanosheets provide numerous advantages. In particular, the methods of the present invention provide a facile and continuous method of making bulk quantities of Janus and Gemini particles. Previous methods of producing such particles involved multiple steps, the use of protecting agents to protect half of the spheres first, and the need to get rid of the agents later.

The amphiphilic nanosheets of the present invention also provide numerous advantages. By way of background, there are opposite effects in the stabilization of Pickering emulsions (emulsions stabilized by particles) using spherical particles. For instance, stabilization requires particles as small as possible. However, smaller particles are easy to escape the interface due to Brownian motion since the adsorption energy to the oil-water interface is proportional to the diameter of the spheres. In fact, it has been found that anisotropic particles with high aspect ratios are better emulsion stabilizers.

As set forth in more detail in the Examples below, the amphiphilic nanosheets of the present invention (such as α-zirconium phosphate platelets) have established a platform for flexible design of multifunctional surfactants tailored for optimal performance. In particular, the highly anisotropic and amphiphilic nanosheets of the present invention reconcile the aforementioned opposite effects due to the existence of length scales, thicknesses, and lateral size ($2R_d$).

The large aspect ratios of the amphiphilic nanosheets also offer optimal stability to the nanosheets between two emulsions to prevent coalescence. Likewise, the nanosheet's large lateral surface area offers strong adsorption energy at the oil-water interface.

Thus, the amphiphilic nanosheets of the present invention provide numerous applications. For instance, the nanosheets can be used as surfactants, paints, cosmetic products, pharmaceutical products, detergents, emulsions, foam stabilizers, rheological thickeners for drilling fluids, and coating agents. In more specific embodiments, the amphiphilic nanosheets of the present invention can be used to enhance the stability of high expansion foam. In various embodiments, such foams may be used for fire extinguishing of liquefied natural gas (LNG). In some embodiments, the amphiphilic nanosheets may be combined with catalysts on one or more surfaces. This may in turn increase the load of catalysts in a particular region, such as reactors.

In further embodiments, the amphiphilic nanosheets of the present invention can used for coating or cleaning solar cells. The amphiphilic nanosheets of the present invention can also be used to deliver drugs, genes, and other compounds to a desired site in an organism (e.g., a human patient). In addition, the amphiphilic nanosheets of the present invention can be used to make luminescent, conductive or semi conductive materials. The amphiphilic nanosheets of the present invention can also be used as alignment agents for biomolecules in magnetic fields using NMR to measure the structure of the biomolecules. Furthermore, the amphiphilic nanosheets can be used to stabilize gas bubbles. Likewise, the amphiphilic nanosheets can be used as contrast agents for ultrasound wave or cosmic waves.

The amphiphilic nanosheets of the present invention can also be used as smart devices. In particular, the grafting of pH- and temperature-sensitive polymers to the nanosheets of the present invention can produce amphiphilic nanosheets suitable for drug delivery and sensor applications. Such amphiphilic nanosheets can be responsive to various environmental conditions, such as temperature fluctuations, changes in pH, and changes in salt concentrations.

In more specific embodiments, the amphiphilic nanosheets of the present invention can be used as surfactants to stabilize various emulsions, such as Pickering emulsions. In further embodiments, the amphiphilic nanosheets of the present invention can be used as surfactants for enhanced oil recovery, such as emulsifiers in microfluidic channels and reservoir rocks (e.g., porous rocks).

The amphiphilic nanosheets of the present invention could also be used to stabilize contrast agents for ultrasonic imaging of colloids, such as gas bubbles. Two-dimensional amphiphiles could be also fabricated by grafting coupling agents over the surface of other materials, such as graphene or $TiO_2$ nanosheets.

Additional Embodiments

Reference will now be made to more specific embodiments of the present disclosure and experimental results that provide support for such embodiments. However, Applicants note that the disclosure below is for exemplary purposes only and is not intended to limit the scope of the claimed invention in any way.

The Examples below pertain to Pickering emulsions stabilized by amphiphilic nano sheets. In particular, in the Examples below, Applicants demonstrate the fabrication of amphiphilic nanosheets, which are either surface- or edge-modified plates with atomic scale thicknesses, the thinnest amphiphilic particles reported so far. The nanosheets are obtained by exfoliation of functionalized layered crystals, the first time that laminar structures have been utilized to produce such particles. Stable emulsions were made utilizing these nanosheets. The adsorption of the amphiphilic nanosheets to the oil-in-water interfaces and the reduction of surface tension between the PDMS and the amphiphilic nanosheet suspensions were quantitatively characterized.

Pickering emulsions are emulsions stabilized by colloidal particles. Water-in-oil Pickering emulsions, formed using solid particles such as asphaltenes, are commonly the reason for the high stability of water droplets in crude oil. As solid particles are adsorbed onto the water-oil interface, the surface energy of the system is reduced and, consequently, the emulsion is established. The stability of Pickering emulsions depends on the size, shape, and wettability of particles at the interface. Based on theory, spherical, acicular, and discotic particles can be used as Pickering stabilizers to produce colloidosomes. Colloidosomes are microcapsules having a coagulated colloidal particle shell that can result from Pickering emulsions, as first synthesized by Velev. For example, platelet-like laponite clay has been used to prepare latex via Pickering miniemulsion polymerization.

Using homogeneous spheres, the highest stability of the resulting Pickering emulsion occurs when the three-phase contact angle among the particle, hydrophobic, and hydrophilic fluids is around 90°. Hydrophobic particles will stabilize water-in-oil emulsions having a contact angle slightly greater than 90°, whereas hydrophilic particles will stabilize oil-in-water emulsions having a contact angle slightly less than 90°. In the case of Janus spheres, the stability is measured using the energy required to remove a particle from equilibrium into the hydrophobic fluid and normalized by the energy of removing it from the hydrophilic fluid, which is the so called Janus balance J, $J=(\sin^2\alpha+2 \cos \theta_p(\cos \alpha-1)/(\sin^2\alpha+2 \cos \theta_\alpha(\cos \alpha+1))$, where $\alpha$ is the angle from the center of the sphere to the hydrophilic-hydrophobic boundary, $\theta_p$ is the contact angle of the hydrophilic side, and $\theta_\alpha$ is the contact angle of the hydrophobic side. The highest stability of the Pickering emulsion stabilized by Janus particles is achieved when J=1, which can be obtained via tuning the parameter $\alpha$.

However, two opposite effects are at work in the stabilization of Pickering emulsions using spherical particles, which have only one length scale, the diameter of the spheres 2r. First, the interfaces of two adjacent emulsions will endure a maximum capillary pressure right before coalescence ($P_c^{max}$), which can be expressed as $P_c^{max}=\pm p (2\gamma_{ow}/r)(\cos \theta \pm z)$, where p is a theoretical parameter used to link the influence of particle concentration (with a "+" sign referring to oil-in-water (o/w) emulsions and with a "−" sign referring to water-in-oil (w/o) emulsions), and z is a constant dependent upon on the arrangement of particles in the interface. $\gamma_{ow}$ is the interfacial energy between the oil and the water, $\theta$ is the three-phase contact angle at the interface and r is the radius of the spheres. Hence, the smaller the size of the spheres, the larger $P_c^{max}$ can be. Spheres with a smaller radius r, therefore, prevent emulsion coalescence better than do larger spheres. Secondly, in the opposite effect, it is well known that small particles tend to escape from the interface by thermal fluctuations. The free energy to, remove a sphere from the interface is defined by $\Delta G_{remove}=\pi r^2 \gamma_{ow}(1+\cos \theta)^2$. Therefore, spheres with a smaller radius r escape more easily from the interface by thermal fluctuation than do the larger spheres.

Figure 1B:
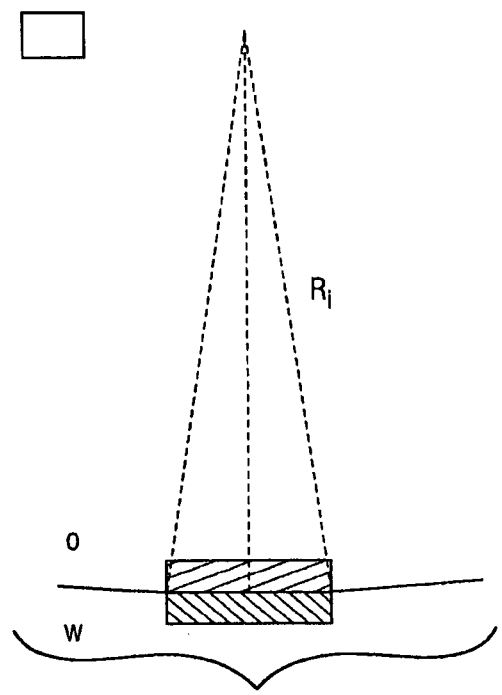

The highly anisotropic particles that Applicants used here could reconcile these two effects due to the existence of two length scales, thickness h and lateral size $2R_d$. A nano sheet in the interface is equivalent to a closed packing of spheres filling the interstitial space, where $2r_s$ (diameter of each sphere) corresponds to the thickness of the nanosheet thickness h. Also, the total area covered by these spheres is equal to the area covered by the nanosheet. The interfaces of two adjacent emulsions will endure a maximum capillary pressure right before coalescence as $P_c^{max} \approx \pm p(2\gamma_{ow}/r_s)(\cos \theta \pm z) \approx \pm p(4\gamma_{ow}/h)(\cos \theta \pm z)$. The nanosheet thickness h can serve as a proxy for sphere diameter in the role of preventing emulsion coalescence. The extremely small value of h offers a good capability to stabilize emulsions. Simultaneously, the nanosheets' large lateral size $2R_d$ offers strong adsorption towards the interface, preventing its escape due to thermal motion. The energy necessary to remove a disk-shaped Janus particle from its equilibrium position at the oil-water interface along the boundary between the hydrophobic and hydrophilic hemispheres is defined by $\Delta G_{min} = \pi R_d^2 (\gamma_{oP1} + \gamma_{wP2} - \gamma_{ow}) + 2\pi R_d (h_1 \gamma_{oP1} + {}_1\gamma_{oP1} + h_2 \gamma_{wP2})$, where $\pi R_d^2$ is the cross-sectional area of the particle, $h_1$ and $h_2$ are thickness of the hydrophobic and the hydrophilic regions, respectively, and the sum of them is equal to the thickness of the disk. $P_1$ indicates the hydrophobic region and $P_2$, the hydrophilic region. $\gamma_{oP1}$ and $\gamma_{wP2}$ are the interfacial energies between the hydrophobic or hydrophilic regions and the oil or water interfaces, respectively. See FIG. 1.

A similar behavior is presented for spherical Janus particles. Thus, particles with a large cross-sectional area, $\pi R_d^2$, can be strongly adsorbed to the interface. Since $\Delta G_{remove} \sim R_d^2$ and $P_c^{max} \sim 1/h$, anisotropic particles with high aspect ratio ($\xi = 2R_d/h$) can be good emulsion stabilizers. In the past, Lagaly et al. confirmed that large-aspect-ratio plate-shaped clay particles together with nonionic surfactants could be used as stabilizers for emulsions by creating a mechanical barrier to prevent coalescence. Additionally, surfactant-free o/w emulsions can be stabilized by synthetic clay (laponites), and, in this case, phase inversion was studied. Here, Applicants report amphiphilic nanosheets that are thin and have large aspect ratios.

Figures 2, 2C:
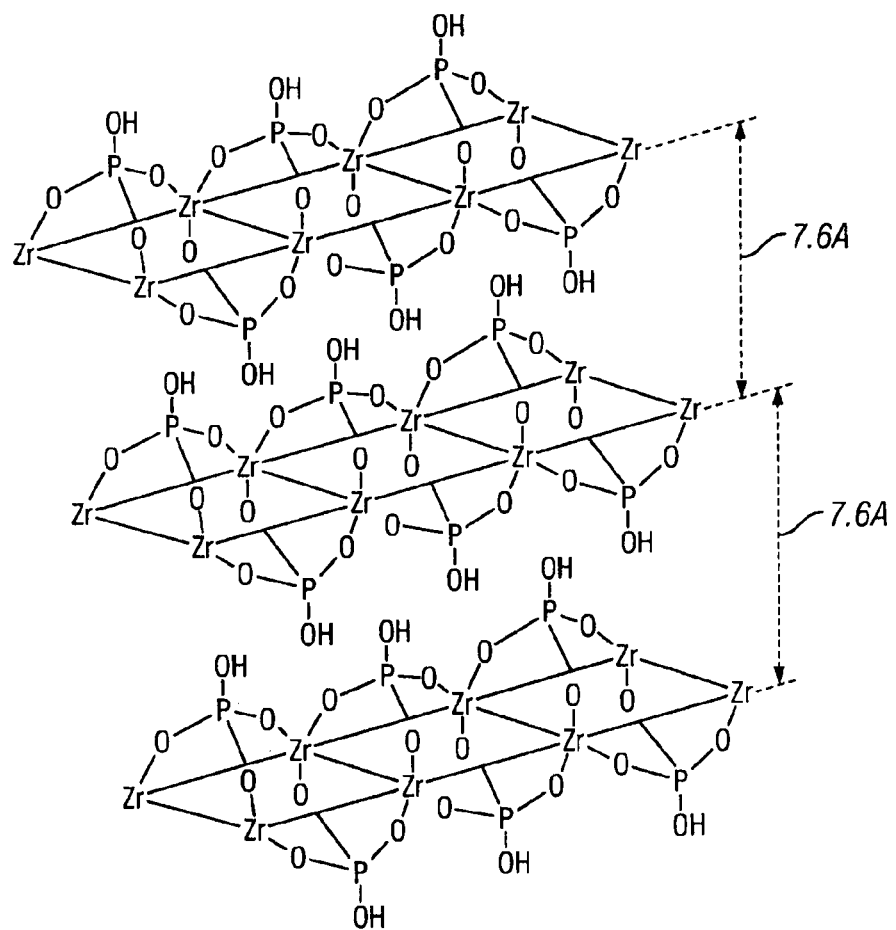

Lamellar crystals are characterized by their layered structure. They can be inorganic crystals, such as clay, α-zirconium phosphates (α-ZrP) (as shown in FIG. 2), niobates, titanates, or organic crystals, such as graphite, which is formed by stacks of graphene layers. Lamellar crystals often exhibit the morphology of nanosheets. See FIG. 2A. They are used as rheological thickeners for drilling fluids, paint, cosmetics, and pharmaceutical products. They have also been extensively investigated in polymer-clay nano-composites and electronics over past decades. They are distinguished by strong bonds in the x and y directions in the plane of the flat crystal, but weaker interactions between the layers in the z direction. Lamellar crystals can, therefore, go through intercalation and exfoliation by guest molecules. When interactions between the intercalated guest molecules are weak enough in the interlayer region, an exfoliation, or separation of layers can take place. Among the most widely used lamellar crystals are the α phase of zirconium phosphate (α-ZrP) with chemical formulas $Zr(HPO_4)_2 \cdot H_2O$. See FIG. 2. The α-ZrP crystal layer is composed of a $ZrO_6$ sheet coordinated with $HPO_4^{2-}$ tetrahedrons forming a covalent network. See FIG. 2C. The thickness of a monolayer of α-ZrP is about 0.66 nm (0.63 nm if the phosphate groups are deprotonated).

Here, Applicants bridge these two thus far independently developing fields of amphiphilic particles and lamellar compounds, demonstrating the ability to create thin amphiphilic nanosheets analogous to Janus (JPs) and Gemini (GPs) nano-plates, which are indeed just the thickness of a single layer of O, P, and Zr atoms, via the functionalization of lamellar crystals followed by exfoliation. In fact, functionalized nanosheets belong to the general category of amphiphilic particles at the "zero" size limit (atomic scale) in one dimension. Within their particle family, they are the closest to conventional surfactant molecules. They are viewed best, however, as assembled clusters of surfactants organized laterally. The single nano-plate layer is rigid when the nanosheet size is about several tenths of a nanometer or less and become flexible when the size is larger than a hundred nanometers, depending on the bending elasticity of the layer. The impermeable nature of the crystalline layer serves as a barrier, preventing diffusion of small molecules, and, hence, the coalescence of emulsions "wrapped" by it.

Example 1

Grafting and Exfoliation of α-ZrP

α-ZrP is characterized by a strong hydrophilicity. Hence, chemical modification is required to convert it to become hydrophobic. First, a coupling agent is grafted over the exposed edges and flat surfaces of the α-ZrP crystals. See FIG. 3 (grafting step). Subsequently, via the exfoliation of these crystals, a mixture of thin-surface and edge-modified amphiphilic nanosheets are obtained from the outer and the inner layers, respectively. See FIG. 3 (exfoliation step) and FIG. 4 (showing the transmission electron microscope (TEM) images of the α-ZrP nanosheets).

As shown in FIG. 4, the α-ZrP nanosheets are thin and flexible, and can present wrinkles, as shown in FIGS. 4B and 4C. This demonstrates that the nanosheets can bend on the oil-water interface to stabilize the emulsions. It has been proven that the single nano-plate layer is rigid when the nanosheet size is about several tenths of a nanometer or less and becomes flexible when the size is larger than a hundred nanometers, depending on the bending elasticity of the layer.

The resulting nano-plates are amphiphilic. Exfoliation of the lamellar crystals occurs when enough tetra-(n-butylammonium) hydroxide ($TBA^+OH^-$) is added to exceed single-layer packing of $TBA^+$ ions in the interlayer region. The mono-layers obtained are atomically flat, mechanically strong, flexible and chemically stable in common basic and acidic solvents. The α-ZrP crystals are easy to synthesize, and the crystal size and size polydispersity are highly tunable by varying phosphoric acid concentration, reaction time, and reaction temperature. In addition, α-ZrP crystals are able to achieve complete exfoliation. See FIG. 5.

It is well known that α-ZrP presents low reactive hydroxyl groups on its surfaces. Although numerous studies have reported intercalation of several compounds into α-ZrP, a direct grafting reaction on ZrP crystal surfaces had not been evaluated consistently, and just a few studies can be found in literature. The surface modification here consists of a chemical (covalent) reaction of the OH groups on the surface of α-ZrP with octadecyl isocyanate (ODI) as a coupling agent.

Figure 6:
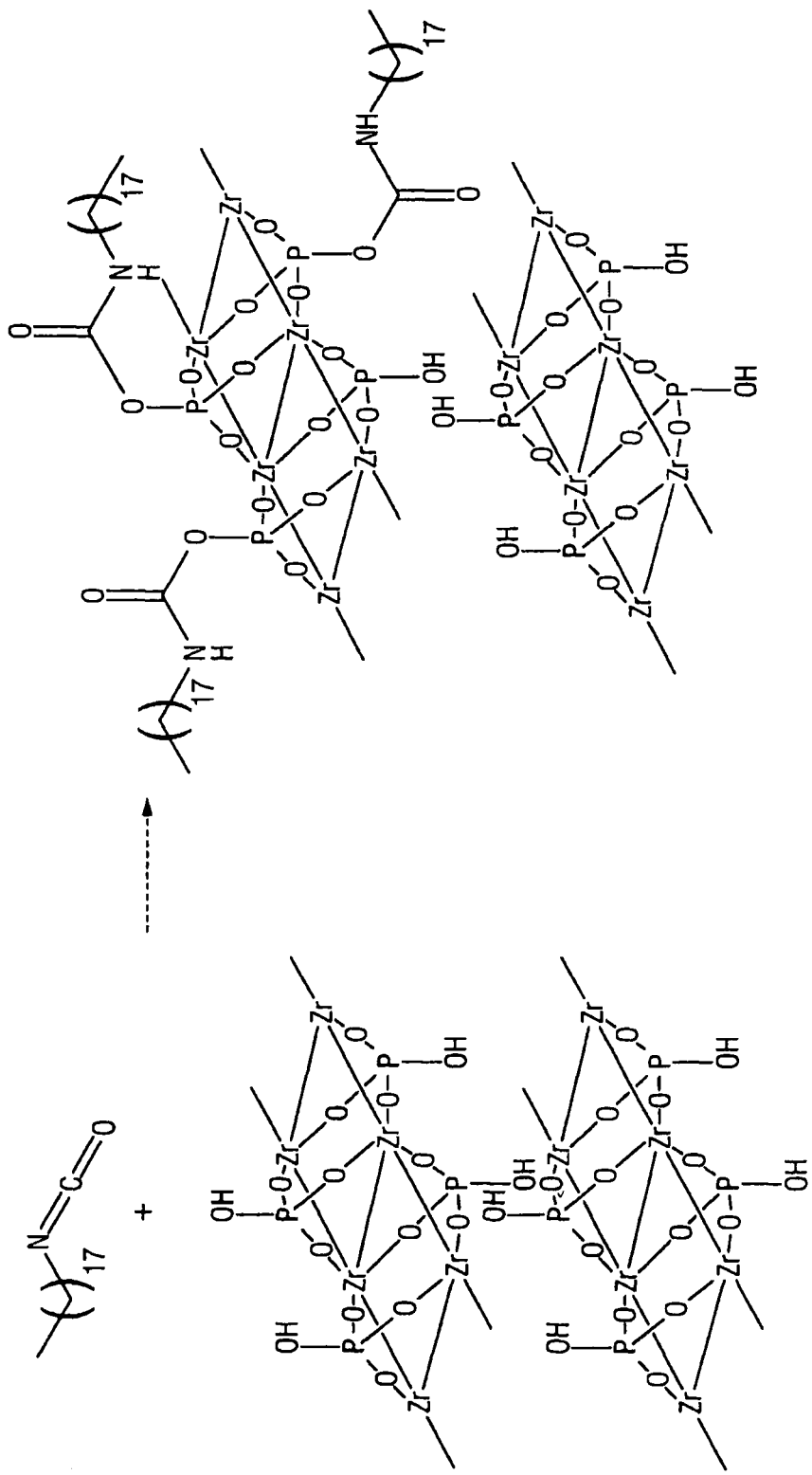
FIG. 6 provides a reaction mechanism for the grafting of octadecyl isocyanate (ODI) to the edges and outer surfaces of α-ZrP crystals.

As illustrated in FIG. 6, the particles created in the current study were synthesized by grafting ODI over the edges and the outer surfaces of α-ZrP crystals. The intercalation of the ODI into α-ZrP does not take place due to the high hydrophobicity of the ODI and the high hydrophilicity of the interlayer region. The ODI coupling agent is one of the most broadly used functional group reagents in synthesis reactions due to the high reactivity of its functional group, —NCO. It has been reported that the isocyanate group reacts with the hydroxyl groups of the hydroxyapatite ($Ca_5(PO_4)_3$ OH) crystals. In fact, the reactivity of the hydroxyapatite surface hydroxyl groups towards the organic isocyanate groups has been confirmed. In addition, previous work also reported the grafting of different organic silane coupling agents on the surface of the calcium phosphate through the reaction with its surface hydroxyl groups.

Example 2

Synthesis and Functionalization of α-ZrPs

The synthesis of the highly crystalline α-ZrP by the hydrothermal method has been described by Sun et al. Sun, L. Y.; Boo, W. J.; Sue, H. J.; Clearfield, A. New *J. Chem.* 2007, 31, 39. Particularly, 6 g $ZrOCl_2 \cdot 8H_2O$ were mixed with 60 mL (9 M) $H_3PO_4$ and heated at 200° C. for 24 h in a high-pressure autoclave. After the reaction, the product was centrifuged and washed three times with deionized (DI) $H_2O$ and dried overnight at 60° C. The dried product was ground with a mortar and pestle into a fine powder. Highly crystalline α-ZrP was used to avoid the intercalation of the modifier in the surface and edge modification step. Finally, the crystals were reacted with octadecyl isocyanate (Aldrich, 98%) in a 1:10 (ODI:ZrP) molar ratio at 65° C., using o-xylene as a solvent, for 12 hours under nitrogen. The resulting product was washed with methanol three times and dried at 60° C. overnight in an oven.

Example 3

Characterization of the Modified α-ZrPs

The resulting powder was characterized by Fourier transform infrared (FTIR, Shimadzu IRAffinity-1 spectrometer in an ATR, attenuated total reflection mode with a ZnSe ATR Prism Model Pike MIRacle A, Columbia, Md.) and thermogravimetric analysis (TGA, Q500 TA Instrument, New Castle, Del.). AFM images were collected with an Agilent/Molecular Imaging PicoSPM coupled with an RHK Technology SPM 1000 Electronics Revision 8, and X-ray photoelectron spectroscopy (XPS, Kratos Axis Ultra Imaging, Chestnut Ridge, N.Y.) to analyze the elementary composition of the final compound.

Fourier Transform Infrared Spectroscopy (FTIR)

Figure 7:
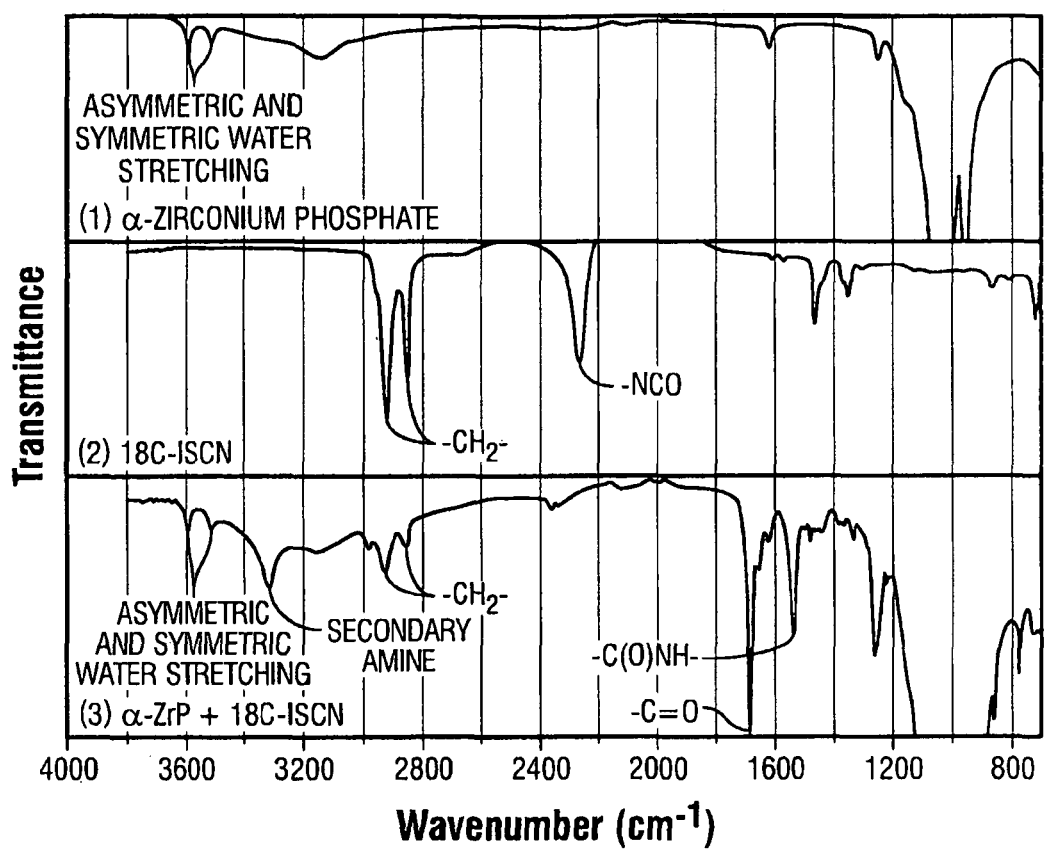
FIG. 7 shows Fourier transform infrared spectroscopy (FTIR) of an α-Zirconium phosphate surface with grafted ODI groups. Graph 1 shows α-ZrP. Graph 2 shows ODI. Graph 3 shows the grafted product.

The grafting reactions (i.e., the outer surface modification reactions) were analyzed by Fourier transform infrared spectroscopy (FTIR). See FIG. 7. The FTIR spectrum of pristine α-ZrP is shown in Graph 1 of FIG. 7. Applicants observed that the isocyanate band (—N≡C≡O) at 2260 $cm^{-1}$ (shown in FIG. 7, Graph 2) vanished after reaction. In the meantime, a new band at 3375 $cm^{-1}$ appeared, which corresponds to a secondary amine (R'R—N—H). See FIG. 7, Graph 3. In addition, the $CH_2$ and $CH_3$ symmetric and asymmetric stretching bands at 3000-2850 $cm^{-1}$ were observed in the product.

FTIR spectra contained two C≡O bands, at 1685 $cm^{-1}$ for the ester carbonyl (—RC(O)O—) and 1525 $cm^{-1}$ for amide II (—RR'C(O)NH), as predicted in FIG. 6. The presence of amide bands and the disappearance of the isocyanate band indicated that the hydroxyl groups over the surface of α-ZrP reacted with the isocyanate groups and resulted in the formation of a urethane linkage. The sharp bands located at 3590 $cm^{-1}$ and 3510 $cm^{-1}$ for pristine α-ZrP and the surface-modified product were attributed to the asymmetric and symmetric stretching of the intercalated water, while the one located at 1620 $cm^{-1}$ was attributed to the bending vibration of water. The remains of the intercalated water, after completion of the grafting reaction, indicated that no intercalation of the lamellar crystals occurred during the grafting reactions because of the high crystallinity of the pristine ZrP crystals.

X-Ray Photoelectron Spectroscopy (XPS)

X-ray photoelectron spectroscopy (XPS) analysis was conducted using a Kratos Axis Ultra Imaging XPS system to measure the film composition that complements the infrared analysis. The binding energy of carbon (C(1s): 285 eV) was used as the reference for data calibration. XPS is a highly diagnostic tool for the assessment of the chemical state of the elements. It has been used before to characterize α-ZrP and its organic derivatives. The XPS spectra of octadecyl isocyanate (ODI) grafted to α-ZrP is shown in FIG. 8. The C(1s) peak located at $E_b$=287.7 eV corresponds to the carbons in the aliphatic chain, and the peak located at 289 eV corresponds to the carbon in the C(O)NH group. See FIG. 8A. As expected, the grafted lamellar crystals displayed a significant N(1s) band. See FIG. 8B. The N(1s) peak located at $E_b1$=399 eV was attributed to the nitrogen in the —C(O)NH group.

In sum, the above FTIR and XPS characterization demonstrated that Applicants have covalently attached an organic coupling agent to the hydroxyl groups of the phosphate on the surfaces of α-ZrP crystals.

Thermogravimetric Analysis (TGA)

FIG. 8C shows the thermogravimetric analysis (TGA) of pristine and grafted crystals. The final product of the thermo-decomposition of pristine α-ZrP is $ZrP_2O_7[Zr(HPO_4)_2 \cdot H_2O(s)+heat\ (700°\ C.) \rightarrow ZrP_2O_7(s)+2H_2O(g)]$ exhibits a weight loss of about 12%. On the other hand, grafted crystals presented a weight loss of about 37%. The TGA spectrum showed four regions. The first one ranged from 25° C. to 91° C.; the second one, from 91° C. to 178° C.; the third one, from 178° C. to 505° C.; and the last one, from 505° C. to 800° C. The first region shows slight loss of solvent from the surface of the crystals. The second region shows evaporation of the water contained between the layers of the α-ZrP. The third region shows the removal of the aliphatic chains grafted on the surface. Finally, the fourth region shows condensation of the phosphates. The TGA indicated that about 25% of sample is from the surface modification.

Example 4

Exfoliation of the Modified α-ZrPs

The functionalized crystals were then exfoliated to obtain a mixture of thin-surface and edge-modified amphiphilic nanosheets. Exfoliated α-ZrP was obtained by adding tetra-(n-butylammonium) hydroxide ($TBA^+OH^-$, Aldrich, 40% in water) at a molar ratio of ZrP:TBA=1:1 in DI water. During the intercalation reaction, the suspension was subject to sonication (Branson 8510, 40 kHz, Danbury, Conn.) to guarantee the intercalation of the $TBA^+$. A complete exfoliation of the crystals might take several minutes to hours. A schematic representation of the α-ZrP crystal exfoliation is depicted in FIG. 3.

Example 5

Use of α-ZrPs in Emulsions

Mineral Oil in Water Emulsions

Applicants' amphiphilic α-ZrP nanosheets have a large aspect ratio (ξ~400) due to their extremely thin thickness (about 2.8 nm). See AFM topography images and section analysis in FIG. 9. As stated before, Applicants predicted that high-aspect ratio nanosheets would be able to offer greater stability between liquid films to prevent coalescence. Their large lateral surface area offers strong adsorption energy at the oil-water interface.

Surfactant-free oil-in-water emulsions stabilized with exfoliated α-ZrP-ODI containing a mixture of surface- and edge-modified amphiphilic nanosheets were prepared at room temperature. The preparation consisted of adding 700 μL of the exfoliated nano-plate suspension (0.05 g/mL) within 2 mL of $H_2O$ and 300 μL of light mineral oil (Sigma Aldrich). The mixture was treated by sonication for 10 minutes to allow the amphiphilic nanosheets move to the oil-water interface. Dye was added to the oil phase to make the oil fluorescent for confocal microscopy observation. Optical and confocal micrographs of the oil-in-water emulsions are shown in FIGS. 10A and 10B, respectively.

A control emulsion was prepared using the same procedure with an exfoliated non-modified α-ZrP suspension. FIGS. 10C and 10F illustrate the oil-water (o/w) emulsion comparison between the use of non-modified and modified α-ZrP as surface-active agents, respectively. The emulsion of the former lasted only for a couple hours, while the latter lasted for months. An optical microscope was used to observe in detail the o/w emulsions.

FIGS. 10D and 10G show the emulsions for both cases when freshly made just after sonication. In the case of FIG. 10G, it should be noted that under white light, the α-ZrP-ODI nanosheets are difficult to observe due to their extreme thin thickness. After 24 days, optical micrographs were obtained for the emulsions. In comparison with FIG. 10D, the control emulsion optical micrograph (FIG. 10E) elucidates coalescence of the oil droplets. The micrographs for the emulsion stabilized using exfoliated α-ZrP-ODI can be found at FIG. 10H (top of the emulsion) and FIG. 10I (middle), where no significant coalescence was observed. In contrast to FIG. 10I, no emulsion droplets were found at the $24^{th}$ day in the middle of the sample shown in FIG. 10C due to the coalescence and creaming in the emulsions made using non-modified α-ZrP nanosheets.

Stabilization of Aromatic Liquids in Water Emulsions

To study the capability of the α-ZrP-ODI nanosheets to emulsify immiscible aromatic liquids, emulsions of toluene-in-water and styrene-in-water were evaluated. For the toluene-in-water emulsions, the droplet size dependence was studied by increasing the amphiphilic nanosheet concentration as Binks et al. did using laponite clay. Ashby, N. P.; Binks, B. P. *Phys. Chem. Chem. Phys.* 2000, 2, 5640.

FIG. 11A displays the toluene droplet diameters for samples with different amounts of α-ZrP-ODI nanosheets. The droplet diameter decreased with an increase in α-ZrP-ODI nanosheets in a range between 0.2 wt % to 0.62 wt %. The droplet diameter became constant at a fixed oil concentration ($\phi_o$=0.085). In general, an increase in amphiphilic nanosheets results in a decrease in toluene droplet size. Also, the toluene-in-water emulsion droplet diameter and the emulsion stability were studied by varying the oil content. FIG. 11B displays the toluene droplet diameters for six samples with varied toluene volume fractions for a fixed α-ZrP-ODI nanosheet concentration (0.45 wt %) over a period of a week. The toluene-in-water emulsion stability was measured for the six samples. All emulsions were stabilized after 100 h. It was found that droplet diameter increased with oil content. See FIG. 11B.

In this experiment, a small size distribution for the droplets was detected, similar to previous Pickering emulsion observations (FIG. 12A). Simply by changing the nanosheet system from α-ZrP-ODI to non-modified α-ZrP nanosheets, we obtained droplets from monodispersed to polydispersed, as shown in FIGS. 12A-B. Visual observations shown in FIG. 12C revealed that the toluene-in-water emulsion stabilized by non-modified nanosheets had undergone a much more evident creaming process than the emulsion stabilized by α-ZrP-ODI nanosheets.

In addition, microscopic images were taken to visually inspect the toluene-in-water emulsions. The image in FIG. 12A illustrates that the toluene droplets are highly uniform. A microscopic image of toluene-in-water emulsions, stabilized by non-modified α-ZrP monolayers as a surfactant, is displayed in FIG. 6B. The image in FIG. 6B had the same composition and had settled for the same amount of time as the samples with α-ZrP-ODI nanosheets in FIG. 6A. Also, in FIG. 6C, creaming is more evident in the toluene-in-water emulsions stabilized by α-ZrP nanosheets (right) compared to that stabilized by α-ZrP-ODI nanosheets (left).

Example 6

Pickering Miniemulsion Polymerization

Figure 13:
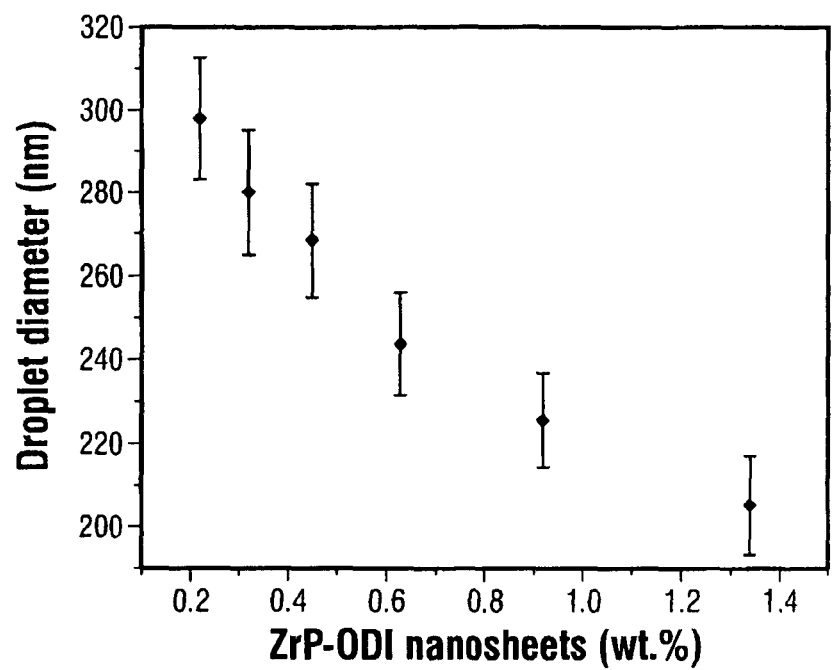
FIG. 13 shows data related to Pickering miniemulsion polymerization of styrene using α-ZrP-ODI nanosheets as stabilizers. Average polystyrene particle diameter is plotted as a function of weight percent of platelets.

The stable Pickering emulsions that Applicants observed above established the viability of producing a Pickering miniemulsion polymerization of styrene using α-ZrP-ODI nanosheets as stabilizers, generating armored latex particles similar to the armored latex suspensions of Bon and Colver. Bon, S. A. F.; Colver, P. J. *Langmuir* 2007, 23, 8316. Applicants performed six Pickering miniemulsion polymerizations of styrene by varying the quantity of α-ZrP-ODI nanosheets from 0.22 to 1.32 wt % in aqueous solutions at a constant monomer volume fraction of styrene, approximately $\phi_o$=0.085. Azobisisobutyronitrile (AIBN, Sigma Aldrich) was used as an initiator for the polymerization. Stable Pickering miniemulsions of submicron α-ZrP-ODI colloidosomes were generated via sonication and were subsequently polymerized at 65° C. for two days. It was observed that polystyrene particle diameter was decreased by increasing the amphiphilic nanosheet content. See FIG. 13.

FIG. 14A shows an SEM image after polymerization of styrene in a Pickering miniemulsion using α-ZrP-ODI nanosheets as stabilizers. The image confirms the formation of polystyrene-α-ZrP-ODI-nanosheets particles with a size 215±52 nm. In addition, TEM images were also taken of the platelet-armored polystyrene particles. See FIGS. 14B-D. FIGS. 8B-C show that styrene emulsions were able to form non-spherical particles showing facet edges and non-smooth corners due to the location of the α-ZrP-ODI nanosheets at the styrene-water interface. Also, as in the case of optical microscopy for mineral oil-in-water and toluene-in-water, observation of the α-ZrP-ODI nanosheets in SEM micrographs is difficult due to their atomic thickness and because the nanosheets were fused on the polystyrene surface. From the TEM micrograph (FIG. 8D), the α-ZrP-ODI nanosheets constituted a layer about 2-nm thick surrounding the polystyrene core.

Evaluation of Surface Coverage

Since styrene emulsification utilized the strong adsorption properties of the nanosheets at the styrene-water interface, the adsorption process was analyzed in a similar way as Bon et al. Bon, S. A. F.; Colver, P. J. *Langmuir* 2007, 23, 8316.

Figure 15:
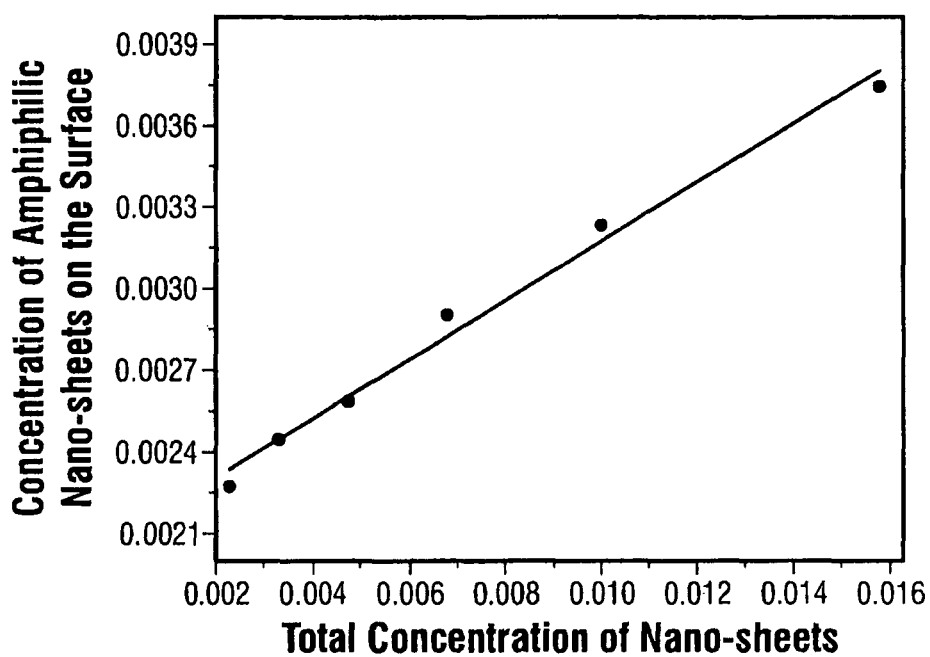
FIG. 15 is plot of the concentration of amphiphilic nanosheets on the surface of polystyrene particle suifaces (CSuiface) as a function of total concentration of platelets (C0).

Calculations were made to determine the amount of platelets on the polystyrene particle surface and the amount of amphiphilic platelets remaining in the continuous phase. The excess concentration was calculated from the following equation: $C_{surface} = 3\pi/2 \; \rho_{ZrP-ODI} \; (_{nanosheets}/\rho_{polystyrene}) \; (h/d_{polystyrene}) \; C_{polystyrene}$, where h is the thickness of the nanosheets, $C_{surface}$ (gg$^{-1}$) is the concentration of amphiphilic nanosheets in the continuous phase, and $C_o$ (gg$^{-1}$) is the total concentration of the amphiphilic nanosheets. $\rho_{ZrP-ODI \; nanosheets}$ and $\rho_{polystyrene}$) are the densities of the ZrP-ODI nanosheets and the polystyrene, respectively. The values of $d_{polystyrene}$, the average diameter of the polystyrene particle suspensions was obtained from FIG. 13. The average diameter of each sample was applied to the equation above to find the surface concentration of α-ZrP-ODI nanosheets. FIG. 15 displays a plot of the α-ZrP-ODI nanosheets on the surface versus the total concentration of α-ZrP-ODI nanosheets. The line of best fit has an $R^2$ value of 0.99, which proves a strong linear relationship. From this relationship, it is demonstrated that the partition, Γ, of the amphiphilic nanosheets on the surface versus in the continuous phase was a constant. By adding more α-ZrP-ODI nanosheets in the emulsions, therefore, surface areas created by these nanosheets produced smaller-sized emulsions (FIG. 13) due to their high surface activity. For a fixed amount of styrene, therefore, the final particle diameter was set by the quantity of amphiphilic nanosheets, M, if the size polydispersity of the resulted particles was not high, because the amount of nanosheets on the surface would be M×Γ, and only a single layer of nanosheet was on the surface. See FIG. 14D.

Example 7

Contact Angle Measurements

Applicants also performed contact angle measurements of the α-ZrP-ODI nanosheets suspensions on polydimethylsiloxane (PDMS) films to determine the surface tension between a hydrophobic surface of PDMS and the amphiphilic nanosheet suspensions. See FIG. 16.

A Phantom V4.2 camera (Vision Research, Wayne, N.J.) with a high-magnification lens, together with the active contours method for measuring high-accuracy contact angles using ImageJ was used to measure the surface tension of the PDMS-water interface. A glass slide was coated with PDMS to simulate similar surface tension interactions as in a PDMS-in-water suspension. The static contact angles were measured for seven different samples at different α-ZrP-ODI nanosheet concentrations, as shown in FIG. 16. Using Young's equation, $Y_{sl} = Y_{sa} - Y_{la} \cos \theta$, where $Y_{sl}$, $Y_{sa}$ and $Y_{la}$ correspond to the PDMS-liquid, PDMS-air and liquid-air surface tensions, respectively. The values taken for $Y_{sa}$ and $Y_{la}$ were 21.8 dyn/cm$^5$ and 72.8 dyn/cm$^6$, respectively. FIG. 16 shows a similar tendency when compared to FIG. 11A and FIG. 13, where α-ZrP-ODI nanosheet concentrations between 0.2 t wt % and 0.62 wt % caused a decrease in surface tension and polystyrene particle diameter.

As α-ZrP-ODI nanosheet concentrations were reduced from 0.2 wt % to 0.6 wt %, the surface tension was also reduced. The reduction of the surface tension was in a good correlation with the emulsion size reduction in the above experiments of toluene and styrene emulsification. Without being bound by theory, this correlation might indicate that the α-ZrP-ODI nanosheets would reduce the oil-water interfacial tension, enabling them to create new surfaces. Without again being bound by theory, the underlying mechanism could be the high flexibility of α-ZrP-ODI nanosheets. See FIG. 4. The nanosheets can curve on to the surface of the oil droplets and make small emulsion droplets. In the case of Gemini nanosheets, the hydrophobic tails can stick into (for the one on the oil side) or bend toward (for the ones on the other side, as the length of the ODI is about 2 nm) the oil phase.

Example 8

Production of Monolayer Films

Monolayer films of the desired alkylsilanes (APTES or OTS) were first prepared on cleaned and oxidized Si(100). Next, ZrP nano-plates (or nanosheets) were deposited through self-assembly using a suspension of the ZrP nanosheets (nanosheets) in a suitable solvent (EtOH for APTES and toluene for OTS). Si(100) substrates were cleaned and hydroxylated with a basic piranha solution (4:1:1 (v:v:v) mixture of high purity $H_2O$: $H_2O_2$(30%): $NH_4OH$) at 80° C. for 30 min. The substrates were rinsed under high-purity water for 60 s, then with ethanol, and finally dried under streaming nitrogen. Then the substrate was incubated in 1 wt % solutions of desired alkylsilanes (APTES or OTS) in a suitable solvent (EtOH for APTES and toluene for OTS) for ca. 15 h. The modified substrates were rinsed under high-purity water for 60 s, then with ethanol, and finally dried under streaming nitrogen. Finally, the ZrP nano-plates (or nanosheets) were deposited through self-assembly using a suspension of the ZrP nanosheets in a suitable solvent (EtOH for APTES and toluene for OTS) for 5 h. The final obtained substrate were rinsed under high-purity water for 60 s, then EtOH, and finally dried under streaming nitrogen. See FIG. 9.

In summary, in the aforementioned Examples, Applicants have demonstrated the fabrication of thin amphiphilic nanosheets by exfoliating α-ZrP crystals grafted with a coupling agent of hydrophobic molecules on their edges and outer surfaces. Their chemical structures were confirmed via XPS, TGA, and FTIR measurements. Octadecyl isocyanate is a powerful functionalization agent to initiate the surface reaction of α-ZrP. Applicants anticipate that this functional group opens doors for further functionalization of α-ZrP to diversify applications. These novel thin amphiphilic nanosheets were used to stabilize surfactant-free oil-in-water emulsions. TEM revealed that there was only a single layer of nanosheets on the interface. Stable uniform toluene-in-water emulsions were observed by using the amphiphilic nanosheets as stabilizers. In contrast, controlled experiments using the non-modified nanosheets produced highly polydispersed emulsions. It confirmed that α-ZrP-ODI nanosheets were attracted to the oil-in-water interface. The polymerization of Pickering miniemulsions to produce polystyrene particles were performed similarly to the method of Bon et al. Bon, S. A. F.; Colver, P. J. *Langmuir* 2007, 23, 8316. From the emulsion size measurements, it was found that the partition Γ of the amphiphilic nanosheets on the surface was constant, and by adding more α-ZrP-ODI nanosheets to the emulsions, surface areas were created by these nanosheets, producing smaller sized emulsions. Applicants also confirmed that the α-ZrP-ODI nanosheets might be able to reduce the oil-in-water surface tension by using nanosheets.

Without further elaboration, it is believed that one skilled in the art can, using the description herein, utilize the present invention to its fullest extent. The embodiments described herein are to be construed as illustrative and not as constraining the remainder of the disclosure in any way whatsoever. While the preferred embodiments have been shown and described, many variations and modifications thereof can be made by one skilled in the art without departing from the spirit and teachings of the invention. Accordingly, the scope of protection is not limited by the description set out above, but is only limited by the claims, including all equivalents of the subject matter of the claims. The disclosures of all patents, patent applications and publications cited herein are hereby incorporated herein by reference, to the extent that they provide procedural or other details consistent with and supplementary to those set forth herein.

What is claimed is:

1. An amphiphilic nanosheet comprising:
   lamellar crystals; and
   a plurality of functional groups appended to the lamellar crystals,
   wherein the lamellar crystals are stacked into layered compounds and exfoliated into layers, wherein the nanosheet comprises at least two regions, a first region and a second region, wherein the first region is hydrophilic, and wherein the second region is hydrophobic, wherein the functional groups comprise octadecyl isocyanate.

2. The amphiphilic nanosheet of claim 1, wherein the lamellar crystals are selected from the group consisting of clays, zirconium phosphates, titanium phosphates, hafnium phosphates, silicon phosphates, germanium phosphates, tin (IV) phosphates, lead (IV) phosphates, niobates, titanates, organic crystals, graphites, graphenes, polyhydroxybutyric acids, and combinations thereof.

3. The amphiphilic nanosheet of claim 1, wherein the lamellar crystals comprise α-zirconium phosphates.

4. The amphiphilic nanosheet of claim 1, wherein the nanosheet has a thickness ranging from about 0.5 nm to about 5 nm.

5. The amphiphilic nanosheet of claim 1, wherein the nanosheet has a diameter ranging from about 10 nm to about 10 μM.

6. The amphiphilic nanosheet of claim 1, wherein the nanosheet has a surface area ranging from about 1 $m^2g^{-1}$ to about 200 $m^2g^{-1}$.

7. The amphiphilic nanosheet of claim 1, wherein the nanosheet has an aspect ratio ranging from about 3500 to about 10.

8. The amphiphilic nanosheet of claim 1, wherein the functional groups are hydrophobic.

9. The amphiphilic nanosheet of claim 1, wherein the functional groups are appended to at least one surface of the lamellar crystals.

10. The amphiphilic nanosheet of claim 1, wherein the functional groups are appended to at least one edge of the lamellar crystals.

11. The amphiphilic nanosheet of claim 1, wherein the appended functional groups are further chemically reacted.

12. The amphiphilic nanosheet of claim 1, wherein the nanosheet is capable of self-assembly.

* * * * *